US008415342B2

(12) United States Patent
Tyle et al.

(10) Patent No.: US 8,415,342 B2
(45) Date of Patent: *Apr. 9, 2013

(54) BESIFLOXACIN OPHTHALMIC COMPOSITION FOR THE TREATMENT OR CONTROL OF INFECTION

(75) Inventors: Praveen Tyle, Pittsford, NY (US); Pramod Kumar Gupta, Pittsford, NY (US); Susan E. Norton, Rochester, NY (US); Lynne Brunner, Webster, NY (US); Joseph Blondeau, Saskatoon (CA)

(73) Assignee: Bausch & Lomb Incorporated, Rochester, NY (US)

( * ) Notice: Subject to any disclaimer, the term of this patent is extended or adjusted under 35 U.S.C. 154(b) by 380 days.

This patent is subject to a terminal disclaimer.

(21) Appl. No.: 12/604,422

(22) Filed: Oct. 23, 2009

(65) Prior Publication Data
US 2010/0105662 A1 Apr. 29, 2010

Related U.S. Application Data

(60) Provisional application No. 61/109,229, filed on Oct. 29, 2008.

(51) Int. Cl.
*A61K 31/55* (2006.01)
*A61K 9/00* (2006.01)
(52) U.S. Cl.
USPC ..................... 514/217.07; 424/400
(58) Field of Classification Search ............. 514/217.07; 424/400
See application file for complete search history.

(56) References Cited

U.S. PATENT DOCUMENTS

| 6,685,958 B2 * | 2/2004 | Roy et al. ........................ 424/427 |
| 2002/0187193 A1 | 12/2002 | Roy et al. |
| 2008/0176834 A1 | 7/2008 | Harms |

FOREIGN PATENT DOCUMENTS

| EP | 0493608 A1 | 7/1992 |
| WO | WO 2008/045673 A2 | 4/2008 |

OTHER PUBLICATIONS

Allen et al., "In vitro activities of mutant prevention concentration-targeted concentrations of fluoroquinolones against *Staphylococcus aureus* in a pharmacodynamic model," Intl J of Antimic Agents, 2004, (vol. 24), (p. 150-160).
Bergogne-Berezin, "Clinical role of protein binding of quinolones," Clin Pharma, 2002, (vol. 41), (Issue. 10), (p. 741-750).
Brook et al., "Anaerobic and aerobic bacteriology of acute conjunctivitis," Annals of Ophthal, Mar. 1979, (p. 389-393).
Chetelat et al., "The photomutagenicity of fluoroquinolones in tests for gene mutation, chromosomal aberration, gene conversion and DNA breakage (Comet assay)," Mutagenesis, 1996, (vol. 11), (Issue. 5), (p. 497-504).
Craig et al., "Protein binding and its significance in antibacterial therapy," Antibac Agents: Pharmacodynamics, Pharmacology, New Agents, Sep. 1989, (vol. 3), (Issue. 3), (p. 407-414).
Diamant et al., "Therapy for bacterial conjunctivitis," Ocular Infections: Update on therapy, Mar. 1999, (vol. 12), (Issue. 1), (p. 15-20).
Drusano, "Role of pharmacokinetics in the outcome of infections," Antimic Agents & Chemo, Mar. 1988, (vol. 32), (Issue. 3), (p. 289-297).
Gocke, "Mechansim of quinolone mutagenicity in bacteria," Mutation Res, 1991, (vol. 248), (p. 135-143).
Gigliotti et al., "Etiology of acute conjunctivitis in children," J of Pediatrics, Apr. 1981, (vol. 98), (Issue. 4), (p. 531-536).
Hammond et al., "Treatment of ocular bacterial infections: an update," J of Amer Opto Assn, Mar. 1997, (vol. 68), (p. 178-187).
Hermsen et al., "Mutant prevention concentrations of ABT-492, levofloxacin, moxifloxacin, and gatifloxacin against three common respiratory pathogens," Antimic Agents & Chemo, Apr. 2005, vol. 49 ( No. 4), p. 1633-1635.
Jensen et al., "In vitro antibiotic susceptibilities of ocular isolates in North and South America," Cornea, 1998, vol. 17 ( No. 1), p. 79-87.
Leeming, "Treatment of ocular infections with topical antibacterials," Clin Pharm, Nov. 1999, vol. 37 ( No. 5), p. 351-360.
Leibowitz, "Antibacterial effectiveness of ciprofloxacin 0.3% ophthalmic solution in the treatment of bacterial conjunctivitis," Amer J of Ophthal, Oct. 1991, p. 29S-33S.
Lorian, "Susceptibility testing of antimicrobials in liquid media," Antibiotics in laboratory medicine, 2005, 4th ed., Lippincott Williams & Wilkins, p. 63-70.
Mukherjee et al., "Ciprofloxacin: mammalian DNA topoisomerase type II poison in vivo," Mutation Res, 1993, p. 87-92.
Merrikin et al., "Effect of protein binding on antibiotic activity in vivo," J of Antimic Chemo, 1983, p. 233-238.
Metzler et al., "Comparison of minimal inhibitory and mutant prevention drug concentrations of 4 fluoroquinolones against clinical isolates of methicillin-susceptible and -resistant *Staphylococcus aureus*," Intl J of Antimic Agents, 2004, p. 161-167.
Nagai et al., "Comparative articular toxicity of garenoxacin, a novel quinolone antimicrobial agent, in juvenile beagle dogs," J of Toxicol Sci, 2002, vol. 27 ( No. 3), p. 219-228.
Nightingale, "Future in vitro and animal studies: development of pharmacokinetic and pharmacodynamic efficacy predictors for tissue-based antibiotics," Pharmacotherapy, 2005, vol. 25 ( No. 12), p. 146S-149S.
Ono et al., "Binding characteristics of fluoroquinolones to synthetic levodopa melanin," J of Pharmacy & Pharmacology, 2003, p. 1127-1133.
Perez et al., "Pharmacokinetics and ocular penetration of grepafloxacin in albino and pigmented rabbits," J of Antimic Chemo, 2002, p. 541-545.
Siefert et al., "Pharmacokinetics of the 8-methoxyquinolone, moxifloxacin: tissue distribution in male rats," J of Antimic Chemo, 1999, p. 61-67.
Smith et al., "Mutant prevention concentrations for single-step fluoroquinolone-resistant mutants of wild-type, efflux-positive, or parC or gyrA mutation-containing *Streptococcus pneumoniae* isolates," Antimic Agents & Chemo, Oct. 2004, vol. 48 ( No. 10), p. 3954-3958.

(Continued)

*Primary Examiner* — Shengjun Wang
(74) *Attorney, Agent, or Firm* — Toan P. Vo

(57) ABSTRACT

A composition comprises besifloxacin in an amount effective for treating or controlling an infection caused by an antibiotic-resistant bacterium. Such a composition can be administered to a subject for the treatment or control of bacterial conjunctivitis caused bay an antibiotic-resistant bacterium.

3 Claims, 6 Drawing Sheets

OTHER PUBLICATIONS

Sheikh et al., "Antibiotics versus placebo for acute bacterial conjunctivitis (review)," The Cochrane Collaboration, 2009, Wiley, No. 4, p. 1-19.

Stahlmann et al., "Toxicity of quinolones," Drugs, 1999, vol. 58 (No. 2), p. 37-42.

Tanaka et al., "Absorption, distribution and excretion of 14C-levofloxacin after single oral administration in albino and pigmented rats: binding characteristics of levofloxacin-related radioactivity to melanin in vivo," J of Pharmacy & Pharmacology, 2004, p. 463-469.

Turnidge, "Pharmacokinetics and pharmacodynamics of fluoroquinolones," Drugs, 1999, vol. 58 (No. 2), p. 29-36.

Wright et al., "Application of fluoroquinolone pharmacodynamics," J of Antimic Chemo, 2000, p. 669-683.

Zeitlinger et al., "Plasma protein binding of fluoroquinolones affects antimicrobial activity," J of Antimic Chemo, 2008, p. 561-567.

Ward et al., "Nonclinical pharmacodynamics, pharmacokinetics, and safety of BOL-303224-A, a novel fluoroquinolone antimicrobial agent for topical ophthalmic use," J of Ocular Pharm & Thera, 2007, (vol. 23), (Issue. 3), (p. 243-256).

Doern et al., "Antimicrobial resistance among clinical isolates of Streptococcus pneumoniae in the United States during 1999-2000, including a comparison of resistance rates since 1994-1995," Antimicrobial Agents and Chemotheraphy, vol. 45, No. 6, Jun. 2001, p. 1721-1729.

Low et al., "Antimicrobial resistance among clinical isolates of Streptococcus pneumoniae in Canada during 2000," Antimicrobial Agents and Chemotherapy, vol. 46, No. 5, May 2002, p. 1295-1301.

* cited by examiner

BESIFLOXACIN OPHTHALMIC COMPOSITION FOR THE TREATMENT OR CONTROL OF INFECTION

CROSS-REFERENCE

This application claims the benefit of Provisional Patent Application No. 61/109,229 filed Oct. 29, 2008 which is incorporated by reference herein.

BACKGROUND

The present invention relates to quinolone composition for the treatment or control of bacterial infection. In particular, the present invention relates to such composition for the treatment or control of infection caused by an antibiotic-resistant bacterium.

Bacterial conjunctivitis is a common external ocular infection that is frequently observed among infants, schoolchildren, and the elderly. The condition is characterized by marked hyperemia or redness of the eye, and mild to moderate purulent conjunctival discharge. Conjunctivitis is contagious and can readily spread within a family, childcare center, or eldercare facility. Children with conjunctivitis may be required to stay home from school or daycare to prevent contagious spread or until they receive treatment for the disease, thus placing a socioeconomic burden on families. Generally, the disease is self-limiting and does not cause permanent loss of vision or structural damage; however, treatment with topical ocular anti-infective agents is standard of care for providing rapid symptomatic relief, reducing the rate of re-infection, possibly preventing the spread of the infection to others, and most importantly, improving the rate of early clinical remission and overall microbial eradication.

The spectrum of causative pathogens continues to evolve, and the incidence of resistance of these organisms to anti-infectives has been increasing. Therefore, there is a continued need for development of novel anti-infectives with improved potency and activity against drug-resistant pathogens.

Some currently available topical anti-infectives for the treatment of bacterial conjunctivitis, such as ofloxacin, ciprofloxacin, levofloxacin, and gatifloxacin, are dosed as frequently as 8 times per day initially and then tapered to 4 times daily (QID) for the remainder of the treatment period. Thus, there is a continued need to provide a treatment of bacterial conjunctivitis at less frequent dosing regimen while enhancing patient convenience. This may be particularly advantageous to parents who must administer treatment to young children.

SUMMARY OF THE INVENTION

The present invention provides a method and composition for treating or controlling bacterial infection caused by antibiotic-resistant bacteria.

In one aspect, such infection is ocular infection.

In another aspect, such infection is bacterial conjunctivitis.

In still another aspect, at least one of such bacteria is methicillin-resistant bacterium.

In a further aspect, at least one of such bacteria is a bacterium resistant to ciprofloxacin, gatfloxacin, or moxifloxacin.

In one embodiment, at least one of such bacteria is ciprofloxacin-resistant bacterium.

In another embodiment, at least one of such bacteria is gatfloxacin-resistant bacterium.

In another embodiment, at least one of such bacteria is moxifloxacin-resistant bacterium.

In yet another aspect, a composition of the present invention comprises besifloxacin ((R)-(+)-(3-amino-2,3,4,5,6,7-hexahydro-1H-azepin-1-yl)-8-chloro-1-cyclopropyl-6-fluoro-1,4,-dihydro-4-oxo-3-quinolinecarboxylic acid; Formula I) and a sustained-release ophthalmic carrier, wherein the composition can provide besifloxacin to the ocular environment for 2, 3, 4, 5, 6, 7, 8, 9, 10 hours or more.

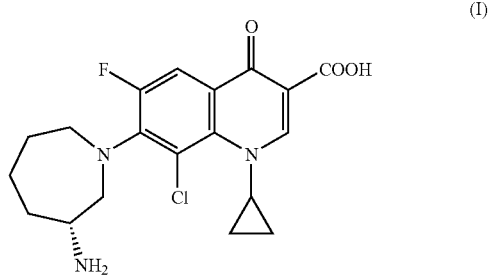 [SMILES: N[C@@H]1CCCCN(c2c(F)cc3c(=O)c(C(=O)O)cn(C4CC4)c3c2Cl)C1]

(I)

In still another aspect, the besifloxacin ophthalmic suspension of the present invention has a favorable benefit/risk profile to support the indication for the treatment of bacterial conjunctivitis in patients 1 year of age and above.

In a further aspect, the proposed dosing regimen for a besifloxacin composition of the present invention is a dosage of 1 drop in an affected eye three times daily (TID) for 5-10 days.

These and other features and advantages of the present invention will be further understood and appreciated by those skilled in the art by reference to the following detailed description and claims and the attached drawings.

DETAILED DESCRIPTION

Efficacy Results

Figure 1:
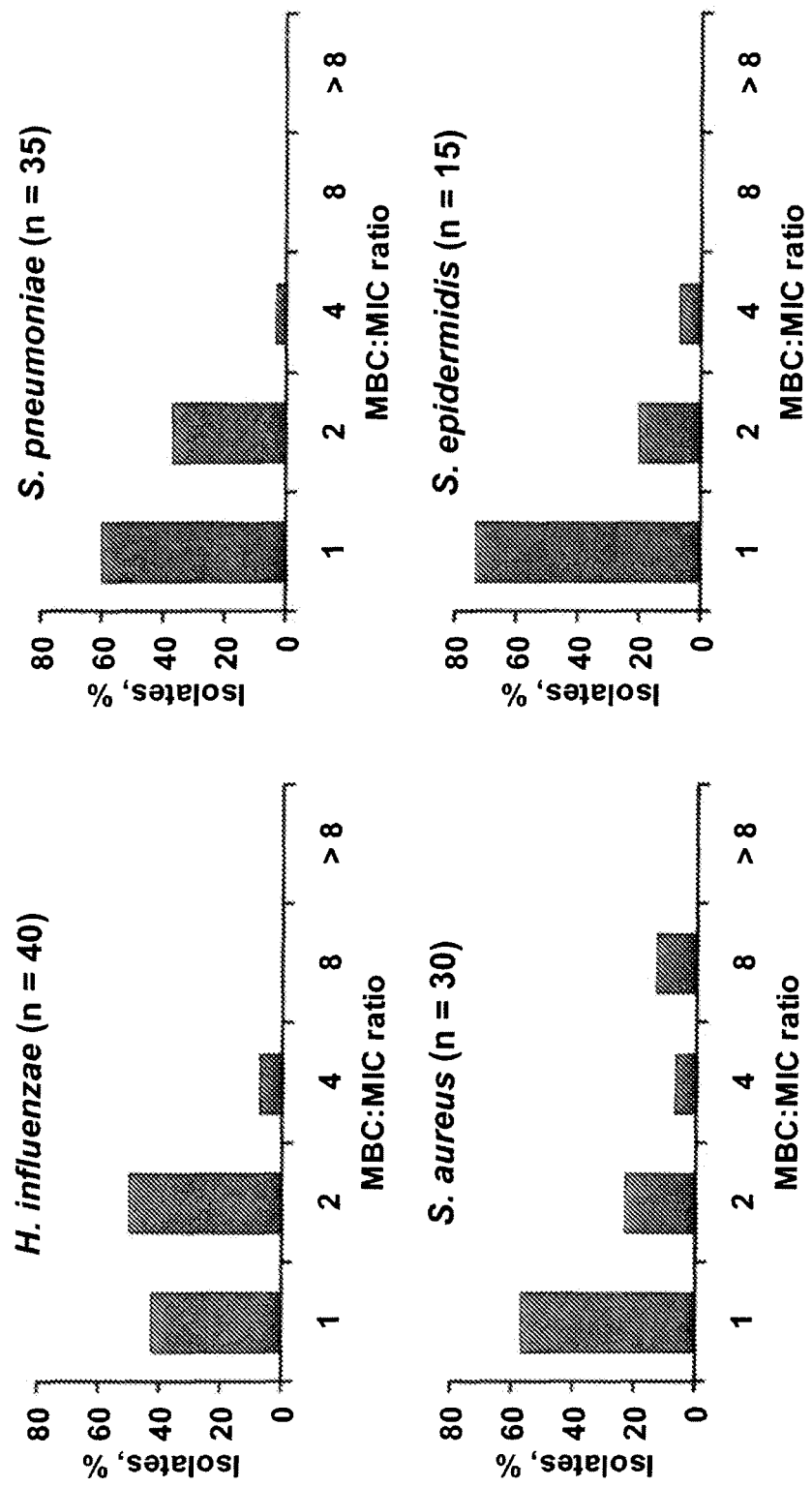
FIG. 1 shows besifloxacin bactericidal activity against recent ocular isolates.

Three large and well-controlled safety and efficacy trials (Studies 373, 433, and 434) were conducted in patients aged 1 to 100 years with a besifloxacin suspension (0.6% weight/volume (w/v)) of the present invention. These studies assessed the clinical and microbial efficacy of this besifloxacin ophthalmic suspension compared with vehicle (Studies 373 and 433) or Vigamox® (Study 434) for the treatment of bacterial conjunctivitis. Results from these studies demonstrated that this besifloxacin ophthalmic suspension administered three times daily (TID) for 5 days was superior to vehicle and non-inferior to Vigamox®. The primary efficacy endpoints were met for each of these studies.

Primary endpoint definitions differed between Study 373 and Studies 433 and 434. The primary efficacy endpoints were clinical resolution and microbial eradication at Visit 3 (Day 8 or 9) for Study 373 and clinical resolution and microbial eradication at Visit 2 (Day 5±1) for Studies 433 and 434. The time point for Visit 2 was defined as Day 4±1 for Study 373 and Day 5±1 for Studies 433 and 434; however, the time point for Visit 3 was defined as Day 8 or 9 in all 3 studies. In addition to the difference in timepoint definitions, the definitions for clinical diagnosis and clinical resolution of bacterial conjunctivitis also differed between Study 373 and Studies 433 and 434. In Study 373, patients were required to present with a minimum of grade 1 for conjunctival discharge and a minimum of grade 1 for either bulbar or palpebral conjunctival injection for a clinical diagnosis of bacterial conjunctivitis. For Studies 433 and 434, a minimum of grade 1 for conjunctival discharge and bulbar conjunctival injection was required for diagnosis of bacterial conjunctivitis. Clinical resolution was defined as the absence of 3 clinical signs (conjunctival discharge, bulbar conjunctival injection, and palpebral conjunctival injection) in Study 373 and 2 clinical signs (conjunctival discharge and bulbar conjunctival injection) in Studies 433 and 434. However, microbial eradication was defined similarly in all 3 studies as the absence of all accepted ocular bacterial species that were present at or above threshold levels at baseline. All patients who were randomly assigned to treatment and had culture-confirmed conjunctivitis were evaluated for the primary endpoints in the intent-to-to treat (ITT) analysis in Study 373 or the modified intent-to-treat (mITT) analysis in Studies 433 and 434.

Study 373-269 patients were randomized to receive besifloxacin ophthalmic suspension (n=137) or vehicle (n=132). A total of 118 (60 besifloxacin and 58 vehicle) patients with culture-confirmed bacterial conjunctivitis at baseline were eligible for the ITT population; efficacy results as follows are data from this ITT, culture-confirmed population. The primary efficacy endpoints of clinical resolution and microbial eradication at Visit 3 (Day 8 or 9) were achieved in a significantly greater percentage of patients who received besifloxacin ophthalmic suspension compared with vehicle. At Visit 3 (Day 8 or 9), the clinical resolution rates for the besifloxacin ophthalmic suspension versus vehicle treatment groups were 61.7% versus 35.7%, respectively (Cochran-Mantel-Haenszel (CMH) adjusted for center effects p=0.0013), based on the absence of 3 clinical signs (conjunctival discharge, bulbar and palpebral conjunctival injection). Microbial eradication rates for the besifloxacin ophthalmic suspension versus vehicle treatment groups were 90.0% vs 69.1%, respectively (CMH adjusted p=0.0041). At Visit 2 (Day 4±1), no statistically significant between-group difference was observed for clinical resolution based on the absence of 3 clinical signs. However, the microbial eradication rates at Visit 2 were significantly greater in the besifloxacin ophthalmic suspension treatment group versus vehicle treatment group (90.0% vs 51.8%, respectively; CMH adjusted p<0.0001).

Study 433-957 patients were randomized to receive besifloxacin ophthalmic suspension (n=473) or vehicle (n=484). A total of 390 (199 besifloxacin and 191 vehicle) patients with culture-confirmed bacterial conjunctivitis were eligible for the mITT population; efficacy results as follows are data from this mITT, as-randomized, culture-confirmed population. The primary efficacy endpoints of clinical resolution and microbial eradication at Visit 2 (Day 5±1) were achieved in a significantly greater percentage of patients who received besifloxacin ophthalmic suspension versus vehicle. At Visit 2 (Day 5±1), the clinical resolution rates for the besifloxacin ophthalmic suspension versus vehicle treatment groups were 45.2% versus 33.0%, respectively (exact Pearson chi-squared test p=0.0169; CMH adjusted p=0.0084). Similarly, microbial eradication rates were significantly higher in the besifloxacin ophthalmic suspension treatment group versus vehicle treatment group (91.5% vs 59.7%; exact Pearson chi-squared test and CMH adjusted p<0.0001). At Visit 3 (Day 8 or 9), the clinical resolution rates in both treatment groups were higher than that observed at Visit 2 (Day 5±1), and the difference between the 2 groups was statistically significant, favoring the besifloxacin ophthalmic suspension treatment group (84.4% vs 69.1%; exact Pearson chi-squared test p=0.0005, CMH adjusted p=0.0011). Moreover, the benefit of besifloxacin ophthalmic suspension over vehicle in eradicating baseline bacterial infections was maintained at Visit 3 (88.4% vs 71.7%; exact Pearson chi-squared test or CMH adjusted p<0.0001).

Study 434-1161 patients were randomized to receive besifloxacin ophthalmic suspension (n=582) or Vigamox (n=579). A total of 533 (252 besifloxacin and 281 Vigamox) patients with culture-confirmed bacterial conjunctivitis were eligible for the mITT, as-treated population; efficacy results as follows are data from this mITT, as-treated, culture-confirmed population. The primary efficacy endpoint analysis of clinical resolution and microbial eradication at Visit 2 (Day 5±1) demonstrated that besifloxacin ophthalmic suspension was non-inferior to Vigamox. At Visit 2 (Day 5±1), besifloxacin ophthalmic suspension was non-inferior to Vigamox® for clinical resolution based on the 95% confidence interval (CI) of the difference (58.3% vs 59.4%, respectively; 95% CI, −9.48%, 7.29%), and there was no statistically significant between-group difference. Besifloxacin ophthalmic suspension also was non-inferior to Vigamox® for microbial eradication based on the 95% CI of the difference (93.3% vs 91.1%, respectively; 95% CI, −2.44%, 6.74%), and there was no statistically significant between-group difference. At Visit 3 (Day 8 or 9), besifloxacin ophthalmic suspension was non-inferior to Vigamox® (based on the 95% CI of the difference) for clinical resolution (84.5% vs 84.0%, respectively; 95% CI, −5.67%, 6.75%) and eradication of baseline bacterial infections (87.3% vs 84.7%, respectively; 95% CI, −3.32%, 8.53%). No statistically significant between-group differences were observed for either of these assessments at Visit 3.

Based on the integrated microbiological data from Studies 373, 433, and 434, the distribution of baseline pathogens was similar across the besifloxacin ophthalmic suspension, vehicle, and Vigamox treatment groups. The relative frequency of the most common organisms isolated at threshold levels or higher from these studies (*H. influenzae, S. pneumoniae, S. aureus,* and *S. epidermidis*) was consistent with common clinical experience in this indication.

Susceptibility testing of clinical trial isolates was performed for besifloxacin and comparator test agents. Overall, isolates cultured in the 3 clinical trials yielded besifloxacin susceptibility patterns similar to those observed in nonclinical studies. A total of 1324 isolates were recovered from culture-confirmed patients in Studies 373, 433, and 434. Overall, $MIC_{50}/MIC_{90}$ values for the 1324 isolates of all species were 0.06/0.25 μg/mL for besifloxacin. Of the 1324 bacterial isolates, 886 (66.9%) were Gram-positive, while the remaining 438 (33.1%) were Gram-negative. The besifloxacin $MIC_{50}/MIC_{90}$ values were 0.06/0.25 μg/mL, for Gram-positive bacteria and 0.03/0.5 μg/mL for Gram-negative bacteria.

Besifloxacin ophthalmic suspension (0.6% (w/v)) was active against a wide range of organisms, including antimicrobial-resistant strains. Overall, the sensitivities of the pathogens to besifloxacin (including various drug-resistant isolates) obtained from patients across all treatment groups were similar. In Studies 373, 433, and 434, susceptibility testing of baseline pathogens confirmed that besifloxacin has potent antimicrobial activity against a wide range of current conjunctivitis pathogens.

Safety Results

Overall, these three studies indicated that a besicomposition of the present invention is safe to be used for topica treatment of ocular infection.

Ocular and systemic pharmacokinetic studies have demonstrated that besifloxacin ophthalmic suspension has high ocular retention ($\geq 1.6$ μg/g in tears for at least 24 hours after a single dose), low systemic exposure (<0.5 ng/mL), and no effect on corneal endothelial cell density.

LIST OF ABBREVIATIONS AND DEFINITION OF TERMS

| Abbreviation | Definition |
|---|---|
| AE | Adverse event |
| AUC | Area under curve |
| ATCC | American Type Culture Collection |
| $C_{max}$ | Maximum concentration |
| CDC | Centers for Disease Control |
| CFU | Colony forming unit |
| CI | Confidence interval |
| CLSI | Clinical Laboratory and Standards Institute |
| CMH | Cochran-Mantel-Haenszel |
| CR | Ciprofloxacin resistant |
| CS | Ciprofloxacin susceptible |
| ERG | Electroretinography |
| FAS | Full analysis set |
| FDA | Food and Drug Administration |
| ITT | Intent-to-treat (population) |
| LC/MS/MS | Liquid chromatography coupled to tandem mass spectrometry |
| LLOQ | Lower limit of quantitation |
| MBC | Minimum bactericidal concentration |
| MIC | Minimum inhibitory concentration |
| mITT | Modified intent-to-treat (population) |
| MPC | Mutant prevention concentration |
| MRSA | Methicillin resistant *S. aureus* |
| MRSE | Methicillin resistant *S. epidermidis* |
| MSSA | Methicillin susceptible *S. aureus* |
| MSSE | Methicillin susceptible *S. epidermidis* |
| NDA | New Drug Application |
| NOAEL | No observable adverse effect level |
| PD | Pharmacodynamic |
| PFGE | Pulsed field gel electrophoresis |
| PK | Pharmacokinetic |
| PP | Per protocol |
| PRSP | Penicillin resistant *S. pneumoniae* |
| PSSP | Penicillin susceptible *S. pneumoniae* |
| QC | Quality control |
| QID | Four times daily |
| QR | Quinolone resistant |
| QS | Quinolone susceptible |
| QT | Electrocardiographic interval of time between the start of Q wave and end of the T wave |
| SAE | Serious adverse event |
| SD | Standard deviation |
| $t_{1/2}$ | Half-life |
| $t_{max}$ | Time to maximum concentration |
| TID | Three times daily |
| VA | Visual acuity |

Overview of Bacterial Conjunctivitis

The globe of the eye is covered by a thin, transparent, mucous membrane called the conjunctiva. The conjunctiva serves to protect the eye and facilitates eye movement by providing lubrication. Conjunctivitis is an inflammation of this lining of the eye.

Bacterial conjunctivitis is a common external ocular infection that is frequently observed among infants, schoolchildren, and the elderly. The condition is characterized by marked hyperemia or redness of the eye, and mild to moderate purulent conjunctival discharge. Conjunctivitis is contagious and can readily spread within a family, childcare center, or eldercare facility. To prevent contagious spread, children with conjunctivitis may be required to stay home from school or daycare until they receive treatment for the disease or the disease resolves, thus placing a socioeconomic burden on families. Generally, the disease is self-limiting and does not cause permanent loss of vision or structural damage (Jensen & Felix, 1998); however, treatment with topical ocular anti-infective agents is standard of care for providing rapid symptomatic relief, improving the rate of early clinical remission and overall microbial eradication, reducing the rate of re-infection, and most importantly, reducing the potential of spreading the infection to others.

Some of the more common causative organisms of bacterial conjunctivitis can be components of the normal lid flora (eg, *Staphylococcus aureus*) or nasopharyngeal flora (eg, *Haemophilus influenzae*) (Brook et al., 1979; Gigliotti et al., 1981; Hammond & Edmondson, 1997; Leeming, 1999). Other common pathogens include *Streptococcus pneumoniae* and *Moraxella* species, but *Neisseria* species, *Corynebacterium* species, and other *Streptococcus* species also may cause bacterial conjunctivitis.

Current Practice for the Treatment of Bacterial Conjunctivitis

Intervention with the use of a topical broad-spectrum ocular anti-infective is the standard of care in the management of bacterial conjunctivitis. Treatment often shortens the duration of the disease, reduces contagious spread, and enhances eradication of causative Gram-positive and Gram-negative organisms (Diamant, 1999; Sheikh & Hurwitz, 2006).

Typically, treatment of bacterial conjunctivitis is based on the likely causative pathogens. The choice of empiric therapy should ensure good activity against both Gram-positive and Gram-negative organisms.

Some currently available topical anti-infective agents for the treatment of bacterial conjunctivitis, such as ofloxacin, gatifloxacin, levofloxacin, and ciprofloxacin, are dosed as frequently as eight times per day initially and then tapered to four times daily (QID) for the remainder of the treatment period. The present formulation was developed to be used as a long-acting topical eye drop that can be dosed three times daily (TID). This less frequent dosing regimen should provide efficacy and enhance patient convenience in the treatment of bacterial conjunctivitis. In addition, the formulation contains an extended-release delivery system that increases the retention/dwell time of the active ingredient on the eye and reduces the rate of loss of medication caused by blinking and tearing. In vitro studies with besifloxacin demonstrated it to have a broad-spectrum antimicrobial effectiveness with potency similar to, if not greater than, antibacterial agents used in other marketed ophthalmic formulations.

Besifloxacin Overview

Chemical Name and Structure

The active moiety of besifloxacin is (R)-(+)-(3-amino-2,3,4,5,6,7-hexahydro-1H-azepin-1-yl)-8-chloro-1-cyclopropyl-6-fluoro-1,4,-dihydro-4-oxo-3-quinolinecarboxylic acid. The molecular formula is $C_{19}H_{21}ClFN_3O_3$ with a molecular weight of 430.30. The structure is illustrated below in Formula I.

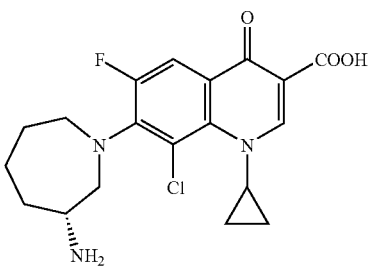
(I)

Formulation

The formulation of the present invention comprises besifloxacin (0.6% (w/v)) suspension, contains the following:

Active ingredient: besifloxacin 0.6% (6 mg/mL)

Inactive ingredients: mannitol, poloxamer 407, and DuraSite (polycarbophil, sodium chloride, ethylenediaminetetraacetic acid disodium, sodium hydroxide, and water). Besifloxacin ophthalmic suspension may have additional sodium hydroxide to adjust pH to approximately 6.5.

Preservative: benzalkonium chloride 0.01%

Although the active ingredient of the foregoing formulation is indicated to be besifloxacin, embodiments of the present invention can include a pharmaceutically (or alternatively, ophthalmically) acceptable salt or ester (such as methyl, ethyl, propyl, isopropyl, tutyl, pentyl, isopentyl, hexyl, or isohexyl ester) of besifloxacin, in place of besifloxacin, that may be suitable or preferred in a particular vehicle.

In addition, substitutes or equivalents for inactive ingredients may be used in different embodiments of the present invention.

For example, mannitol may be replaced by, or used in addition to, sorbitol, xylitol, erythritol, dextrose, glucose, glycerol, propylene glycol, or a combination thereof. In one aspect, these compounds are used to provide a tonicity adjustment (tonicity-adjusting agents). Such tonicity-adjusting agents may be used in concentrations sufficient to adjust the tonicity of the composition to the range of about 200-400 mOsm/kg (alternatively, about 200-350 mOsm/kg, or 250-350 mOsm/kg, or 250-320 mOsm/kg, or 275-325 mOsm/kg, or 275-300 mOsm/kg).

Poloxamer 407, a non-ionic surfactant, may be replaced by, or used in addition to, another non-ionic or ionic surfactant, such as tyloxapol, polysorbates, triglycerides, hydrogenated castor oil (including polyethoxylated castor oil), polyethylene glycols (such as PEG 400, PEG 800, PEG 1000, or PEG 3500). Such a surfactant may be included in concentrations of about 0.01-10% by weight of the composition (alternatively, about 0.01-5%, or 0.01-2%, or 0.01-1%, or 0.1-5%, or 0.1-2%, or 0.1-1%, or 0.1-0.5%, or 0.2-2% by weight of the composition).

Polycarophil may be replaced by, or used in addition to, cellulose derivatives (such as carboxymethyl cellulose or hydroxypropylmethyl cellulose), polyvinyl pyrrolidone, polysccharides (such as alginate, hyaluronate, gellan, dextran, or xanthan gum), or other polyacrylic acid derivatives. Such a polymer, polysaccharide, or cellulose may be included in the composition at concentration Ethylenediaminetetraacetic acid disodium may be replaced by, or used in addition to, an organic phosphonic acid salt or a polyaminocarboxylic acid r salt (e.g., ethylenediaminetetraacetic acid (EDTA), hexamethylenediaminetetraacetic acid (HMDTA), N-(2-hydroxyethyl)ethylenediamine-N,N',N'-triacetic acid (HEEDTA or HEDTA), hydroxymethylethylenediaminetriacetic acid (HMEDTA), 1,3-diamino-2-propanol-N,N,N',N'-tetracetic acid, 1,3-diamino-2-propane-N,N,N',N'-tetracetic acid, ethylene glycol-bis(2-aminoethylether)-N,N,N',N'-tetraacetic acid, ethylenediamine-N,N-diacetic acid (EDDA), or diethylenetriaminepentaacetic acid (DTPA)). Such a chelating agent may be used in the composition in concentrations of about 0.01-2% by weight of the total weight of the composition (alternatively, about 0.01-1%, or 0.01-0.5%, 04 0.1-0.5%, or 0.1-1%, or 0.1-2%, or 0.5-2%, or 0.5-1% by weight)

Bezakonium chloride may be replaced by, or used in addition to, another preservative, such as polyquat-1, polyquat-42, stabilized oxychloro complex, hydrogen peroxide (or a source thereof). A preservative may be used in concentrations of about 0.001-0.5% by weight of the composition (alternatively, about 0.001-0.1%, or 0.01-0.1%, or 0.01-0.05% by weight), depending on the type of the preservative. In certain embodiments for single use, the preservative may be eliminated from the formulation.

Dosage and Administration

In one aspect, the present formulation can be administered at a dose of 1 drop per affected eye TID for 5 days. Each drop can have a volume in the range of 15-35 μL.

In another aspect, the present formulation can be administered at a dose of 1 drop per affected eye TID for 6, 7, or up to 10 days.

Nonclinical Evaluation of Besifloxacin

Microbiology

Mechanism of Action

Besifloxacin is an 8-chloro fluoroquinolone with an N–1 cyclopropyl group. The substituents of the side chain at the 7 position and the chlorine at the 8 position, along with the standard fluoroquinolone core, provide besifloxacin its unique structure and unique activity profile. The compound has broad-spectrum activity against aerobic, facultative, and anaerobic Gram-positive and Gram-negative bacteria due to the inhibition of two essential bacterial enzymes, DNA gyrase and topoisomerase IV. DNA gyrase introduces negative supercoils into DNA during replication and translation, while topoisomerase IV is required for partitioning of the chromosomal DNA during bacterial cell division. Fluoroquinolones, such as besifloxacin, result in the formation of double-stranded DNA breaks that cannot be repaired, leading ultimately to bacterial cell death. Besifloxacin is bactericidal with minimum bactericidal concentrations (MBCs) generally within one dilution of the minimum inhibitory concentrations (MICs). The mechanism of action of fluoroquinolones, including besifloxacin, is different from that of aminoglycoside, macrolide, tetracycline, β-lactam, sulfonamide, and cyclic peptide antibacterial drugs. Therefore, besifloxacin may be active against pathogens that are resistant to these antibacterials and these antibacterial drugs may be active against pathogens that are resistant to besifloxacin.

The mechanism of action of besifloxacin was evaluated in an in vitro study that compared besifloxacin to ciprofloxacin and moxifloxacin for catalytic inhibition as well as cleavable complex stimulation with DNA gyrase and topoisomerase IV purified from representative Gram-positive and Gram-negative bacterial pathogens. Catalytic inhibition and cleavable complex stimulation by besifloxacin was 4- to 16-fold more potent than ciprofloxacin and moxifloxacin against *S. pneumoniae* DNA gyrase and 2.5- to 5.0-fold more potent than ciprofloxacin and moxifloxacin against *S. pneumoniae* topoisomerase IV (Table 1). In assays with purified *E. coli* DNA gyrase and topoisomerase IV, both catalytic inhibition and cleavable complex stimulation by besifloxacin were equivalent to that of the ciprofloxacin and moxifloxacin comparators.

Furthermore, an experiment was conducted to assess the mechanism of action of besifloxacin in *S. pneumoniae*, *S. aureus*, and *E. coli* via step selections for isolates with decreased susceptibility to besifloxacin, as well as by testing for altered susceptibilities of ciprofloxacin-resistant variants of all three species containing genetically defined mutations in the quinolone resistance determining regions (QRDRs) of structural genes encoding DNA gyrase and topoisomerase IV (Table 2). Results from this experiment were consistent with well-established mechanisms of action and target-based resistance to other fluoroquinolone inhibitors of type II DNA topoisomerases, including ciprofloxacin, levofloxacin, gatifloxacin, moxifloxacin, and gemifloxacin. DNA sequencing of mutants with altered besifloxacin susceptibilities as well as the MIC testing against ciprofloxacin-resistant isolates indicated that besifloxacin targets DNA gyrase and topoisomerase IV in representative Gram-positive and Gram-negative isolates, with evidence for balanced activity against both essential type II DNA topoisomerase targets in streptococci and staphylococci.

TABLE 1

Inhibitory Activity (IC$_{50}$) and Potency of Besifloxacin and Comparators in Stabilizing the Cleavable Complex (CC$_{25}$) of *S. pneumoniae* and *E. coli* DNA Gyrases and Topoisomerase IV

| Quinolones | *S. pneumoniae* enzymes | | | | *E. coli* enzymes | | | |
| --- | --- | --- | --- | --- | --- | --- | --- | --- |
| | IC$_{50}$ | | CC$_{25}$ | | IC$_{50}$ | | CC$_{25}$ | |
| | Gyrase | Topo IV | Gyrase | Topo IV | Gyrase | Topo IV | Gyrase | Topo IV |
| Ciprofloxacin | | | | | | | | |
| μM | 40 | 5 | 40-80 | 2.5-5 | 1 | 27 | 0.15 | 1.5 |
| μg/mL | 15 | 2 | 15-25 | 1-2 | 0.3 | 9 | 0.05 | 0.5 |
| Moxifloxacin | | | | | | | | |
| μM | 10 | 2.5 | 10-20 | 2.5 | 1.6 | 20 | 0.2 | 2.3 |
| μg/mL | 4 | 1 | 4-8 | 1.5 | 0.7 | 9 | 0.07 | 1 |
| Besifloxacin | | | | | | | | |
| μM | 2.5 | 1 | 2.5 | 1 | 2.3 | 23 | 0.1 | 1.4 |
| μg/mL | 1 | 0.4 | 1 | 0.4 | 1 | 10 | 0.04 | 0.6 |

Topo IV = Topoisomerase IV.
CC$_{25}$ is the drug concentration that produces 25% linearization of the DNA under the reaction conditions used.

TABLE 2

MICs (μg/mL) of Besifloxacin Against Defined Topoisomerase Mutants

| Topoisomerase mutants | Besifloxacin | Ciprofloxacin | Moxifloxacin |
| --- | --- | --- | --- |
| *S. pneumoniae* | | | |
| Wild type | 0.12 | 1 | 0.25 |
| parC S79Y | 0.25 | 8 | 0.25 |
| gyrA S81F | 0.5 | 1 | 0.5 |
| parC S79Y + gyrA S81F | 1 | 64 | 4 |
| *S. aureus* | | | |
| Wild type | 0.03 | 1 | 0.06 |
| parC S80F (or E84K) | 0.06 | 8 | 0.5 |
| parC S80F + gyrA S84L | 0.5 | 64 | 2 |

TABLE 2-continued

MICs (μg/mL) of Besifloxacin Against Defined Topoisomerase Mutants

| Topoisomerase mutants | Besifloxacin | Ciprofloxacin | Moxifloxacin |
| --- | --- | --- | --- |
| *E. coli* | | | |
| Wild type | 0.12 | 0.008 | 0.06 |
| gyrA D87Y (or S83L) | 0.5 | 0.12 | 0.5 |
| gyrB D426N | 0.5 | 0.03 | 0.12 |
| gyrA S83L + parE H445L | 1 | 0.12 | 0.5 |
| gyrA S83L + parC S80R | 16 | 4 | 4 |

Development of Resistance to Besifloxacin

Besifloxacin is a potent antibacterial agent by virtue of its efficient biochemical inhibition of type II bacterial topoisomerases at low micromolar levels. Besifloxacin was associated with a low mutant prevention concentration (MPC), especially in the two Gram-positive pathogens, *S. aureus* and *S. pneumoniae*, in which the MPCs were only four times higher than the MICs for those organisms. Correspondingly, very few drug-resistant mutants were obtained in in vitro experiments for those two species (<1 mutant per $10^{10}$ cells).

Consistent with these results is a dual-targeting mechanism of action for besifloxacin, especially in *S. aureus* and *S. pneumoniae*. Dual targeting indicates that DNA gyrase (encoded by gyrA and gyrB) and topoisomerase IV (encoded by parC and parE) are both inhibited by besifloxacin. As a consequence, strains with high-level resistance would only emerge if both targets were mutated simultaneously, an event that is not very likely in strains that lack predisposing mutations. A dual-targeting mechanism of action for besifloxacin is supported by the following experimental evidence:

In *S. aureus* and *S. pneumoniae*, single (1st step) mutants were extremely rare (<1/$10^{10}$ cells) and only few or no double (2nd step) mutants were obtained (Table 3).

Single mutations in the gyrA or in the parC gene were obtained in *S. aureus* as well as in *S. pneumoniae*. In both species, MIC values for the gyrA and the parC mutants different by no more than one 2-fold serial dilution, indicating that besifloxacin has no preference for one enzyme over the other. By comparison, all single mutations in quinolone-resistant strains of *E. coli* were mapped to either the gyrA or the gyrB gene consistent with the general finding that quinolones primarily target the DNA gyrase in Gram-negative bacteria.

Biochemical experiments with the purified DNA gyrase and topoisomerase IV enzymes from *S. pneumoniae* and *E. coli* were performed. Inhibitory concentrations of besifloxacin for the *E. coli* gyrase were 10-fold lower than for the topoisomerase IV, suggesting a modest preference for DNA gyrase from Gram-negative bacteria. In contrast, the difference between the inhibitory concentrations for DNA gyrase and topoisomerase IV from *S. pneumoniae* was only 2.5-fold, suggesting that besifloxacin targets both enzymes in Gram-positive bacteria.

TABLE 3

In Vitro Multistep Selection for Besifloxacin-Resistant Mutants

| Species | Selection step | MIC (µg/mL) | MSW (µg/mL) | MPC (µg/mL) | Mutation rate at 4 × MIC |
|---|---|---|---|---|---|
| *S. pneumoniae* | 1st step | 0.12 | 0.12-0.25 | 0.5 | $<7 \times 10^{-10}$ |
| | 2nd step | 0.5 | 0.5-2 | 2-4 | $2.4 \times 10^{-8}$ |
| *S. aureus* | 1st step | 0.03 | 0.03-0.06 | 0.12 | $3.3 \times 10^{-10}$ |
| | 2nd step | 0.25 | NMO | 0.25 | NMO |
| *E. coli* | 1st step | 0.12 | 0.12-2 | 4 | $3.8 \times 10^{-8}$ |
| | 2nd step | 2 | 2-8 | 16 | $6 \times 10^{-9}$ |

MIC = Minimum inhibitory concentration;
MSW = Mutant Selection Window;
MPC = Mutant prevention concentration;
NMO = No mutants obtained.

Bactericidal Activity of Besifloxacin

The success of in vivo antimicrobial action depends to a large extent on the host's defense mechanisms, which ultimately sequester and kill the microorganisms that have been reduced by the bacteriostatic/bactericidal action of the antibacterial agent. Thus, it is also of interest to profile the bactericidal activity of antimicrobial agents. The assessment of in vitro bactericidal activity can be accomplished in multiple ways, for example, the time-kill method or the determination of the minimum bactericidal concentration (MBC). The MBC is the drug concentration that leads to a $\geq 99.9\%$ reduction in the viable count (CFU/mL) of the test organism after 24 hours. Bactericidal agents are characterized by low MBC:MIC ratios.

FIG. 1 and Table 4 illustrate the besifloxacin bactericidal activity against recent ocular isolates. Besifloxacin MBCs within 1 to 2 dilutions of the MIC (MBC:MIC ratios $\leq 2$) were observed for the majority of ocular isolates tested (*S. pneumoniae*, *S. epidermidis*, *H. influenzae*, and *S. aureus*). Besifloxacin MBCs were within 4-fold of the MIC for more than 80% of the isolates tested. Among staphylococci, equivalent besifloxacin MBC:MIC ratios were observed for both ciprofloxacin-susceptible and ciprofloxacin-resistant isolates, as well as for methicillin-susceptible and methicillin-resistant isolates. The MBC:MIC ratios observed with besifloxacin were similar to that for comparator fluoroquinolones. Against the majority of ocular isolates tested, the MBC did not exceed 2-fold the initial MIC, indicating a bactericidal mode of action for besifloxacin. In contrast to all other comparator agents tested (moxifloxacin, azithromycin, tobramycin, gatifloxacin, and ciprofloxacin; data for the latter three not shown), only besifloxacin yielded measurable MIC and MBC values within the test range for all isolates. Time-kill studies confirmed the bactericidal activity of besifloxacin against *S. aureus*, *S. pneumoniae*, and *H. influenzae* (data not shown).

TABLE 4

In Vitro activity and MBC:MIC Ratio of Besifloxacin and Comparator Agents Against Recent Ocular Isolates
Species (no. of isolates)

| Test drug | MIC (µg/mL) | | | | % of isolates with MBC:MIC ratio | | | | | |
|---|---|---|---|---|---|---|---|---|---|---|
| | Range | $MIC_{50}$ | $MIC_{90}$ | % S[a] | 1 | 2 | 4 | 8 | $\geq 16$ | n[b] |
| *H. influenzae* (N = 40) | | | | | | | | | | |
| Besifloxacin | $\leq$0.004-0.03 | 0.015 | 0.015 | na | 42.5 | 50.0 | 7.5 | 0.0 | 0.0 | 40 |
| Moxifloxacin | 0.008-0.03 | 0.015 | 0.03 | 100.0 | 60.0 | 37.5 | 2.5 | 0.0 | 0.0 | 40 |
| Azithromycin | $\leq$0.004-2 | 0.5 | 1 | 100.0 | 15.8 | 57.9 | 15.8 | 7.9 | 2.6 | 38 |
| *S. aureus* (N = 30) | | | | | | | | | | |
| Besifloxacin | 0.015-4 | 0.12 | 4 | na | 56.7 | 23.3 | 6.7 | 13.3 | 0.0 | 30 |
| Moxifloxacin | 0.015->8 | 0.06 | >8 | 56.7 | 64.0 | 16.0 | 4.0 | 16.0 | 0.0 | 25 |
| Azithromycin | 0.5->8 | 1 | >8 | 53.3 | 0.0 | 11.1 | 11.1 | 22.2 | 55.6 | 9 |
| *S. epidermidis* (N = 15) | | | | | | | | | | |
| Besifloxacin | 0.015-4 | 0.03 | 4 | na | 73.3 | 20.0 | 6.7 | 0.0 | 0.0 | 15 |
| Moxifloxacin | 0.03->8 | 0.06 | >8 | 60.0 | 66.7 | 25.0 | 8.3 | 0.0 | 0.0 | 12 |
| Azithromycin | 0.12->8 | >8 | >8 | 26.7 | 0.0 | 33.3 | 0.0 | 0.0 | 66.7 | 3 |
| *S. pneumoniae* (N = 35) | | | | | | | | | | |
| Besifloxacin | 0.015-0.5 | 0.06 | 0.06 | na | 60.0 | 37.1 | 2.9 | 0.0 | 0.0 | 35 |
| Moxifloxacin | 0.03-2 | 0.06 | 0.12 | 97.1 | 51.4 | 40.0 | 8.6 | 0.0 | 0.0 | 35 |
| Azithromycin | 0.06->8 | 0.06 | >8 | 62.9 | 64.0 | 4.0 | 24.0 | 8.0 | 0.0 | 25 |

Note:
This study included, where applicable, isolates that were beta-lactamase positive or resistant to oxacillin, penicillin, and/or ciprofloxacin.
[a]Percent of susceptible isolates based on CLSI guidelines.
[b]n: number of isolates for which measurable MBC and MIC values were obtained, and thus, an MBC:MIC ratio could be calculated. The n value was used as the baseline (100%) for the calculation of the percentage of isolates with MBC:MIC ratio.
na: not applicable since no systemic susceptibility breakpoints have been established for besifloxacin.

In conclusion, besifloxacin showed bactericidal activity against target pathogens associated with bacterial conjunctivitis, demonstrating activity greater than or equivalent to that of other currently marketed fluoroquinolones against these organisms.

Antibacterial Spectrum of Activity of Besifloxacin

The antibacterial spectrum of activity of besifloxacin was evaluated against a variety of clinical isolates in in vitro studies using standard Clinical Laboratory and Standards Institute (CLSI) reference methods. MIC provides an estimate of the inhibitory activity of antimicrobial agents. The MIC, when determined using standard reference methods, is a reproducible parameter for a given antimicrobial agent against most rapidly growing pathogens. Except where noted, MIC values were determined by broth microdilution methods.

Tables 5, 6, and 7 summarize antibacterial activities of besifloxacin and comparator antibacterials against representative Gram-positive, Gram-negative, and anaerobic pathogens associated with human ocular infections. Table 8 further summarizes besifloxacin antibacterial activity data pooled across multiple nonclinical studies. Overall, results from these studies show that besifloxacin has potent antibacterial activity against a very broad spectrum of bacteria, including all species commonly isolated from patients with bacterial conjunctivitis, such as *Streptococcus* spp., *Staphylococcus* spp., *Haemophilus* spp., *Corynebacterium* spp., and *Moraxella* spp. In addition, besifloxacin is active against a variety of Gram-positive, Gram-negative, and anaerobic pathogens associated with ocular infections. The data demonstrate that the antibacterial potency of besifloxacin is similar to or exceeds the potency of the fluoroquinolone and non-fluoroquinolone comparator antibacterials.

TABLE 5

Activity of Besifloxacin and Comparators Against Gram-positive Bacteria

| Test drug[a] | Species (phenotype, no. of isolates) MIC (µg/mL) | | | | Test drug[a] | Species (phenotype, no. of isolates) MIC (µg/mL) | | | |
|---|---|---|---|---|---|---|---|---|---|
| | Range | $MIC_{50}$ | $MIC_{90}$ | % S[b] | | Range | $MIC_{50}$ | $MIC_{90}$ | % S[b] |
| *Staphylococcus aureus* (all phenotypes, N = 30) | | | | | *Staphylococcus aureus* (CNS, N = 16) | | | | |
| Besifloxacin | 0.015-4 | 0.12 | 4 | na | Besifloxacin | 0.03-4 | 0.25 | 4 | na |
| Moxifloxacin | 0.015->8 | 0.06 | >8 | 56.7 | Moxifloxacin | 0.06->8 | 1 | >8 | 18.8 |
| Gatifloxacin | 0.03->8 | 1 | >8 | 46.7 | Gatifloxacin | 0.12->8 | 2 | >8 | 6.3 |
| Ciprofloxacin | 0.12->8 | 2 | >8 | 46.7 | Ciprofloxacin | 2->8 | 8 | >8 | 0.0 |
| Azithromycin | 0.5->8 | 1 | >8 | 53.3 | Azithromycin | 0.5->8 | >8 | >8 | 43.8 |
| Tobramycin | 0.12->32 | 0.5 | >32 | 80.0 | Tobramycin | 0.25->32 | 0.5 | >32 | 68.8 |
| Levofloxacin | 0.06->8 | 1 | >8 | 50.0 | Levofloxacin | 0.25->8 | 4 | >8 | 12.5 |
| Oxacillin | 0.12->8 | 0.25 | >8 | 63.3 | Oxacillin | 0.12->8 | 0.5 | >8 | 50.0 |
| *Staphylococcus aureus* (MSSA, N = 19) | | | | | *Staphylococcus epidermidis* (all phenotypes, N = 15) | | | | |
| Besifloxacin | 0.015-4 | 0.015 | 0.25 | na | Besifloxacin | 0.015-4 | 0.03 | 4 | na |
| Moxifloxacin | 0.015->8 | 0.06 | 1 | 68.4 | Moxifloxacin | 0.03->8 | 0.06 | >8 | 60.0 |
| Gatifloxacin | 0.03->8 | 0.06 | 2 | 63.2 | Gatifloxacin | 0.06->8 | 0.06 | >8 | 60.0 |
| Ciprofloxacin | 0.12->8 | 0.5 | 8 | 57.9 | Ciprofloxacin | 0.12->8 | 0.12 | >8 | 60.0 |
| Azithromycin | 0.5->8 | 1 | >8 | 78.9 | Azithromycin | 0.12->8 | >8 | >8 | 26.7 |
| Tobramycin | 0.12-8 | 0.25 | 1 | 94.7 | Tobramycin | ≤0.008-16 | 0.06 | 8 | 86.7 |
| Levofloxacin | 0.06->8 | 0.25 | 4 | 68.4 | Levofloxacin | 0.12->8 | 0.12 | >8 | 60.0 |
| Oxacillin | 0.12-0.5 | 0.25 | 0.5 | 100.0 | Oxacillin | ≤0.06-4 | 1 | 2 | 40.0 |
| *Staphylococcus aureus* (MRSA, N = 11) | | | | | *Staphylococcus epidermidis* (MSSE, N = 6) | | | | |
| Besifloxacin | 0.015-4 | 0.5 | 4 | na | Besifloxacin | 0.015-0.25 | 0.03 | na | na |
| Moxifloxacin | 0.03->8 | 1 | >8 | 36.4 | Moxifloxacin | 0.03-2 | 0.06 | na | 83.3 |
| Gatifloxacin | 0.06->8 | 2 | >8 | 18.2 | Gatifloxacin | 0.06-1 | 0.06 | na | 83.3 |
| Ciprofloxacin | 0.12->8 | >8 | >8 | 27.3 | Ciprofloxacin | 0.12->8 | 0.12 | na | 83.3 |
| Azithromycin | 0.5->8 | >8 | >8 | 9.1 | Azithromycin | 0.12->8 | 0.5 | na | 66.7 |
| Tobramycin | 0.5->32 | 1 | >32 | 54.5 | Tobramycin | ≤0.008-0.06 | 0.03 | na | 100.0 |
| Levofloxacin | 0.12->8 | 4 | >8 | 18.2 | Levofloxacin | 0.12-8 | 0.12 | na | 83.3 |
| Oxacillin | 8->8 | >8 | >8 | 0.0 | Oxacillin | ≤0.06-0.12 | ≤0.06 | na | 100.0 |
| *Staphylococcus aureus* (CS, N = 14) | | | | | *Staphylococcus epidermidis* (MRSE, N = 9) | | | | |
| Besifloxacin | 0.015-0.25 | 0.015 | 0.12 | na | Besifloxacin | 0.015-4 | 0.25 | na | na |
| Moxifloxacin | 0.015-0.06 | 0.03 | 0.06 | 100.0 | Moxifloxacin | 0.03->8 | 1 | na | 44.4 |
| Gatifloxacin | 0.03-1 | 0.06 | 0.25 | 92.9 | Gatifloxacin | 0.06->8 | 1 | na | 44.4 |
| Ciprofloxacin | 0.12-0.5 | 0.25 | 0.5 | 100.0 | Ciprofloxacin | 0.12->8 | 2 | na | 44.4 |
| Azithromycin | 0.5->8 | 1 | >8 | 64.3 | Azithromycin | >8->8 | >8 | na | 0.0 |
| Tobramycin | 0.12-8 | 0.25 | 1 | 92.9 | Tobramycin | 0.03-16 | 4 | na | 77.8 |
| Levofloxacin | 0.06-2 | 0.12 | 0.25 | 92.9 | Levofloxacin | 0.12->8 | 2 | na | 44.4 |
| Oxacillin | 0.12->8 | 0.25 | >8 | 78.6 | Oxacillin | 1-4 | 1 | na | 0.0 |
| *Staphylococcus epidermidis* (CS, N = 9) | | | | | *Staphylococcus lugdunensis* (N = 15) | | | | |
| Besifloxacin | 0.015-0.03 | 0.03 | na | na | Besifloxacin | 0.015-2 | 0.06 | 0.5 | na |
| Moxifloxacin | 0.03-0.06 | 0.06 | na | 100.0 | Moxifloxacin | 0.03->8 | 0.12 | 2 | 73.3 |
| Gatifloxacin | 0.06-0.06 | 0.06 | na | 100.0 | Gatifloxacin | 0.03-8 | 0.12 | 2 | 73.3 |
| Ciprofloxacin | 0.12-0.12 | 0.12 | na | 100.0 | Ciprofloxacin | 0.06->8 | 0.12 | >8 | 66.7 |
| Azithromycin | 0.25->8 | >8 | na | 33.3 | Azithromycin | 0.25->8 | >8 | >8 | 46.7 |
| Tobramycin | ≤0.008-8 | 0.03 | na | 88.9 | Tobramycin | 0.03->32 | 0.12 | 32 | 60.0 |
| Levofloxacin | 0.12-0.12 | 0.12 | na | 100.0 | Levofloxacin | 0.06->8 | 0.25 | >8 | 66.7 |
| Oxacillin | ≤0.06-2 | 0.12 | na | 55.6 | Oxacillin | ≤0.06->8 | 0.5 | >8 | 60.0 |

TABLE 5-continued

Activity of Besifloxacin and Comparators Against Gram-positive Bacteria

| Test drug[a] | Species (phenotype, no. of isolates) MIC (μg/mL) | | | | Test drug[a] | Species (phenotype, no. of isolates) MIC (μg/mL) | | | |
|---|---|---|---|---|---|---|---|---|---|
| | Range | $MIC_{50}$ | $MIC_{90}$ | % S[b] | | Range | $MIC_{50}$ | $MIC_{90}$ | % S[b] |
| *Staphylococcus epidermidis* (CNS, N = 6) | | | | | *Staphylococcus saprophyticus* (N = 101) | | | | |
| Besifloxacin | 0.25-4 | 0.25 | na | na | Besifloxacin | 0.015-0.25 | 0.06 | 0.12 | na |
| Moxifloxacin | 1->8 | 2 | na | 50.0 | Moxifloxacin | 0.03-0.25 | 0.12 | 0.12 | 100.0 |
| Gatifloxacin | 1->8 | 1 | na | 50.0 | Gatifloxacin | 0.03-0.25 | 0.12 | 0.25 | 100.0 |
| Ciprofloxacin | 2->8 | >8 | na | 0.0 | Ciprofloxacin | 0.06-0.5 | 0.25 | 0.5 | 100.0 |
| Azithromycin | 0.12->8 | >8 | na | 16.7 | Azithromycin | 0.12->8 | 1 | >8 | 54.5 |
| Tobramycin | 0.06-16 | 2 | na | 83.3 | Tobramycin | ≦0.008-32 | 0.015 | 0.06 | 99.0 |
| Levofloxacin | 2->8 | 8 | na | 0.0 | Levofloxacin | 0.06-0.5 | 0.5 | 0.5 | 100.0 |
| Oxacillin | 0.12-4 | 1 | na | 50.0 | Oxacillin | ≦0.06->8 | 0.5 | 1 | 9.9 |
| *Staphylococcus haemolyticus* (N = 101) | | | | | *Staphylococcus warneri* (N = 50) | | | | |
| Besifloxacin | 0.015-4 | 0.5 | 1 | na | Besifloxacin | 0.015-2 | 0.06 | 1 | na |
| Moxifloxacin | 0.015->8 | 1 | 8 | 39.6 | Moxifloxacin | 0.015->8 | 0.06 | 4 | 76.0 |
| Gatifloxacin | 0.03->8 | 2 | 8 | 40.6 | Gatifloxacin | 0.03->8 | 0.12 | 4 | 76.0 |
| Ciprofloxacin | 0.06->8 | >8 | >8 | 37.6 | Ciprofloxacin | 0.06->8 | 0.25 | >8 | 74.0 |
| Azithromycin | 0.25->8 | >8 | >8 | 26.7 | Azithromycin | 0.12->8 | >8 | >8 | 34.0 |
| Tobramycin | 0.015->32 | 2 | 32 | 64.4 | Tobramycin | 0.015->32 | 0.06 | 8 | 86.0 |
| Levofloxacin | 0.06->8 | 4 | >8 | 39.6 | Levofloxacin | 0.06->8 | 0.12 | >8 | 76.0 |
| Oxacillin | ≦0.06->8 | >8 | >8 | 31.7 | Oxacillin | ≦0.06->8 | 0.5 | >8 | 46.0 |
| *Staphylococcus hominis* (N = 50) | | | | | *Streptococcus agalactiae* (N = 100) | | | | |
| Besifloxacin | 0.015-2 | 0.25 | 1 | na | Besifloxacin | 0.03-0.12 | 0.06 | 0.06 | na |
| Moxifloxacin | 0.03->8 | 1 | 4 | 34.0 | Moxifloxacin | 0.06-1 | 0.12 | 0.25 | na |
| Gatifloxacin | 0.03->8 | 1 | 4 | 32.0 | Gatifloxacin | 0.12-1 | 0.25 | 0.25 | 100.0 |
| Ciprofloxacin | 0.06->8 | 8 | >8 | 30.0 | Ciprofloxacin | 0.5-8 | 0.5 | 1 | na |
| Azithromycin | 0.12->8 | >8 | >8 | 16.0 | Azithromycin | 0.015->8 | 0.06 | >8 | 73.0 |
| Tobramycin | 0.015->32 | 16 | 32 | 32.0 | Tobramycin | 8->128 | 32 | 64 | na |
| Levofloxacin | 0.06->8 | 8 | >8 | 30.0 | Levofloxacin | 0.25-4 | 0.5 | 1 | 98.0 |
| Oxacillin | ≦0.06->8 | >8 | >8 | 16.0 | Penicillin | ≦0.015-0.06 | 0.03 | 0.06 | 100.0 |
| *Streptococcus pneumoniae* (all phenotypes, N = 35) | | | | | *Streptococcus pyogenes* (N = 101) | | | | |
| Besifloxacin | 0.015-0.5 | 0.06 | 0.06 | na | Besifloxacin | 0.03-0.06 | 0.03 | 0.06 | na |
| Moxifloxacin | 0.03-2 | 0.06 | 0.12 | 97.1 | Moxifloxacin | 0.06-0.5 | 0.12 | 0.25 | na |
| Gatifloxacin | 0.015-4 | 0.12 | 0.25 | 97.1 | Gatifloxacin | 0.06-0.5 | 0.12 | 0.25 | 100.0 |
| Ciprofloxacin | 0.03->8 | 0.5 | 1 | 91.4 | Ciprofloxacin | 0.12-2 | 0.5 | 0.5 | na |
| Azithromycin | 0.06->8 | 0.06 | >8 | 62.9 | Azithromycin | 0.03->8 | 0.06 | 8 | 85.1 |
| Tobramycin | 8-32 | 16 | 32 | na | Tobramycin | 4-64 | 16 | 16 | na |
| Levofloxacin | 0.5-8 | 0.5 | 1 | 97.1 | Levofloxacin | 0.25-2 | 0.5 | 0.5 | 100.0 |
| Penicillin | ≦0.015->4 | ≦0.015 | 4 | 88.6 | Penicillin | ≦0.015-0.06 | ≦0.015 | ≦0.015 | 100.0 |
| *Streptococcus pneumoniae* (PSSP, N = 31) | | | | | Lancefield group C, F, G *streptococci* (N = 50) | | | | |
| Besifloxacin | 0.015-0.5 | 0.06 | 0.06 | na | Besifloxacin | 0.015-0.25 | 0.03 | 0.06 | na |
| Moxifloxacin | 0.03-2 | 0.06 | 0.12 | 96.8 | Moxifloxacin | 0.03-1 | 0.12 | 0.12 | na |
| Gatifloxacin | 0.015-4 | 0.12 | 0.25 | 96.8 | Gatifloxacin | 0.06-2 | 0.12 | 0.25 | 98.0 |
| Ciprofloxacin | 0.03->8 | 0.5 | 1 | 90.3 | Ciprofloxacin | 0.12->8 | 0.5 | 0.5 | na |
| Azithromycin | 0.06->8 | 0.06 | >8 | 67.7 | Azithromycin | 0.008->8 | 0.06 | >8 | 74.0 |
| Tobramycin | 8-32 | 16 | 32 | na | Tobramycin | 2-32 | 8 | 16 | na |
| Levofloxacin | 0.5-8 | 0.5 | 1 | 96.8 | Levofloxacin | 0.12-8 | 0.5 | 0.5 | 98.0 |
| Penicillin | ≦0.015-0.5 | ≦0.015 | 0.25 | 100.0 | Penicillin | ≦0.015-0.06 | ≦0.015 | 0.06 | 100.0 |
| *Streptococcus pneumoniae* (PISP, N = 2) | | | | | *Viridans streptococci*[c] (N = 156) | | | | |
| Besifloxacin | 0.06-0.12 | na | na | na | Besifloxacin | 0.015-2 | 0.06 | 0.12 | na |
| Moxifloxacin | 0.12-0.12 | na | na | 100.0 | Moxifloxacin | 0.03-4 | 0.12 | 0.25 | na |
| Gatifloxacin | 0.25-0.25 | na | na | 100.0 | Gatifloxacin | 0.03-8 | 0.25 | 0.5 | na |
| Ciprofloxacin | 0.5-1 | na | na | 100.0 | Ciprofloxacin | 0.12->8 | 1 | 4 | na |
| Azithromycin | >8->8 | na | na | 0.0 | Azithromycin | 0.008->8 | 0.06 | >8 | 53.2 |
| Tobramycin | 16-32 | na | na | na | Tobramycin | 0.5-128 | 16 | 32 | na |
| Levofloxacin | 0.5-1 | na | na | 100.0 | Levofloxacin | 0.12->8 | 1 | 1 | 95.5 |
| Penicillin | 4-4 | na | na | 0.0 | Penicillin | ≦0.015->4 | 0.06 | 1 | 76.3 |
| *Streptococcus pneumoniae* (PRSP, N = 2) | | | | | | | | | |
| Besifloxacin | 0.03-0.06 | na | na | na | | | | | |
| Moxifloxacin | 0.06-0.25 | na | na | 100.0 | | | | | |
| Gatifloxacin | 0.12-0.25 | na | na | 100.0 | | | | | |
| Ciprofloxacin | 0.5-1 | na | na | 0.0 | | | | | |
| Azithromycin | 0.06->8 | na | na | 50.0 | | | | | |

TABLE 5-continued

Activity of Besifloxacin and Comparators Against Gram-positive Bacteria

Species (phenotype, no. of isolates) MIC (μg/mL)

| Test drug[a] | Range | MIC$_{50}$ | MIC$_{90}$ | % S[b] |
|---|---|---|---|---|
| Tobramycin | 16-32 | na | na | na |
| Levofloxacin | 0.5-1 | na | na | 100.0 |
| Penicillin | >4->4 | na | na | 0.0 |

[a]MSSA: methicillin susceptible *S. aureus*, MRSA: methicillin resistant *S. aureus*, MSSE: methicillin susceptible *S. epidermidis*, MRSE: methicillin resistant *S. epidermidis*, CS: ciprofloxacin susceptible, PSSP: penicillin susceptible *S. pneumoniae*, PISP: penicillin intermediate *S. pneumoniae*, PRSP: penicillin resistant *S. pneumoniae*, VSE: vancomycin susceptible *enterococci*, VRE: vancomycin resistant *enterococci*

[b]Percent of susceptible isolates. Clinical and Laboratory Standards Institute's breakpoints were not available for some antibacterials for the interpretation as susceptible, intermediate, or resistant.

[c]Viridans group *streptococci* consisted of 2 *S. anginosus*, 13 *S. bovis*, 7 *S. constellatus*, 28 *S. intermedius*, 51 *S. mitis*, 22 *S. oralis*, 2 *S. salivarius*, 17 *S. sanguis*, and 14 other viridans group species.

na = Not applicable.

TABLE 6

Activity of Besifloxacin and Comparators Against Gram-negative Bacteria

| Test drug[a] | Range | MIC$_{50}$ | MIC$_{90}$ | % S[b] | Test drug[a] | Range | MIC$_{50}$ | MIC$_{90}$ | % S[b] |
|---|---|---|---|---|---|---|---|---|---|
| *Citrobacter koseri* (N = 100) | | | | | *Klebsiella oxytoca* (N = 50) | | | | |
| Besifloxacin | 0.03->8 | 0.06 | 0.25 | na | Besifloxacin | 0.06-8 | 0.12 | 1 | na |
| Levofloxacin | 0.015->8 | 0.03 | 0.12 | 99.0 | Levofloxacin | 0.015-8 | 0.03 | 0.5 | 90.0 |
| Moxifloxacin | 0.015->8 | 0.03 | 0.25 | na | Moxifloxacin | 0.03-8 | 0.06 | 2 | na |
| Gatifloxacin | 0.008->8 | 0.015 | 0.12 | 99.0 | Gatifloxacin | 0.015-8 | 0.03 | 0.5 | 92.0 |
| Ciprofloxacin | 0.004->8 | 0.008 | 0.06 | 99.0 | Ciprofloxacin | 0.008->8 | 0.015 | 0.5 | 90.0 |
| Tobramycin | 0.25-16 | 0.5 | 1 | 99.0 | Tobramycin | 0.25-8 | 0.5 | 1 | 96.0 |
| Azithromycin | 2->8 | 8 | >8 | na | Azithromycin | 8->8 | >8 | >8 | na |
| Ceftazidime | 0.06-4 | 0.12 | 0.5 | 100.0 | Ceftazidime | 0.03-1 | 0.12 | 0.5 | 100.0 |
| *Haemophilus influenzae* (all phenotypes, N = 40) | | | | | *Legionella pneumophila* (N = 50) | | | | |
| Besifloxacin | ≤0.004-0.03 | 0.015 | 0.015 | na | Besifloxacin | 0.015-0.06 | 0.03 | 0.03 | na |
| Moxifloxacin | 0.008-0.03 | 0.015 | 0.03 | 100.0 | Levofloxacin | 0.015-0.06 | 0.03 | 0.03 | na |
| Gatifloxacin | ≤0.004-0.015 | 0.008 | 0.008 | 100.0 | Moxifloxacin | 0.015-0.06 | 0.03 | 0.06 | na |
| Ciprofloxacin | 0.008-0.015 | 0.008 | 0.008 | 100.0 | Gatifloxacin | 0.015-0.06 | 0.03 | 0.06 | na |
| Azithromycin | ≤0.004-2 | 0.5 | 1 | 100.0 | Ciprofloxacin | 0.015-0.06 | 0.03 | 0.03 | na |
| Tobramycin | 0.06-4 | 2 | 4 | na | Tobramycin | 0.25-4 | 1 | 2 | na |
| Levofloxacin | 0.008-0.015 | 0.015 | 0.015 | 100.0 | Azithromycin | 0.03-1 | 0.12 | 1 | na |
| *Haemophilus influenzae* (bla negative, N = 24) | | | | | *Moraxella catarrhalis* (N = 101) | | | | |
| Besifloxacin | ≤0.004-0.03 | 0.015 | 0.015 | na | Besifloxacin | 0.015-0.12 | 0.03 | 0.03 | na |
| Moxifloxacin | 0.008-0.03 | 0.015 | 0.03 | 100.0 | Levofloxacin | 0.015-0.5 | 0.015 | 0.03 | 100.0 |
| Gatifloxacin | ≤0.004-0.015 | 0.008 | 0.008 | 100.0 | Moxifloxacin | 0.015-0.12 | 0.03 | 0.03 | na |
| Ciprofloxacin | 0.008-0.015 | 0.008 | 0.015 | 100.0 | Gatifloxacin | 0.008-0.25 | 0.015 | 0.015 | na |
| Azithromycin | ≤0.004-2 | 0.5 | 2 | 100.0 | Ciprofloxacin | 0.008-0.25 | 0.015 | 0.015 | 100.0 |
| Tobramycin | 0.06-4 | 2 | 4 | na | Tobramycin | 0.03-0.5 | 0.25 | 0.25 | na |
| Levofloxacin | 0.008-0.015 | 0.015 | 0.015 | 100.0 | Azithromycin | 0.015-0.06 | 0.03 | 0.03 | 100.0 |
| | | | | | Oxacillin | 0.25->8 | 4 | 8 | na |
| *Haemophilus influenzae* (bla positive, N = 16) | | | | | *Morganella morganii* (N = 51) | | | | |
| Besifloxacin | 0.008-0.03 | 0.015 | 0.03 | na | Besifloxacin | 0.03->8 | 0.12 | 4 | na |
| Moxifloxacin | 0.008-0.03 | 0.03 | 0.03 | 100.0 | Levofloxacin | 0.015->8 | 0.06 | 8 | 76.5 |
| Gatifloxacin | ≤0.004-0.015 | 0.008 | 0.008 | 100.0 | Moxifloxacin | 0.03->8 | 0.25 | >8 | na |
| Ciprofloxacin | 0.008-0.015 | 0.008 | 0.008 | 100.0 | Gatifloxacin | 0.015->8 | 0.12 | >8 | 74.5 |
| Azithromycin | 0.06-1 | 0.5 | 1 | 100.0 | Ciprofloxacin | 0.004->8 | 0.015 | >8 | 76.5 |
| Tobramycin | 0.5-4 | 2 | 2 | na | Tobramycin | 0.25-32 | 1 | 4 | 90.2 |
| Levofloxacin | 0.015-0.015 | 0.015 | 0.015 | 100.0 | Azithromycin | 8->8 | >8 | >8 | na |
| | | | | | Ceftazidime | 0.03->32 | 0.12 | 16 | 82.4 |

[a]bla: beta-lactamase

[b]Percent of susceptible isolates. Clinical and Laboratory Standards Institute's breakpoints were not available for some antibacterials for the interpretation as susceptible, intermediate, or resistant.

na = Not applicable.

TABLE 7

Activity of Besifloxacin and Comparators Against Anaerobic Bacteria

| Test drug | Range | MIC$_{50}$ | MIC$_{90}$ | % S[a] | Test drug | Range | MIC$_{50}$ | MIC$_{90}$ | % S[a] |
|---|---|---|---|---|---|---|---|---|---|
| *Bacteroides fragilis* (N = 20) | | | | | *Prevotella* spp. (N = 20) | | | | |
| Besifloxacin | 0.25-2 | 0.5 | 1 | na | Besifloxacin | 0.06-16 | 1 | 4 | na |
| Moxifloxacin | 0.25-8 | 0.5 | 2 | 95.0 | Moxifloxacin | 0.12->16 | 4 | 8 | 45.0 |
| Gatifloxacin | 1-16 | 2 | 4 | na | Gatifloxacin | 0.25->16 | 8 | 16 | na |
| Clindamycin | 0.5->8 | 2 | >8 | 65.0 | Clindamycin | ≦0.03->8 | ≦0.03 | >8 | 85.0 |
| Metronidazole | 2-2 | 2 | 2 | 100.0 | Metronidazole | 0.25-8 | 4 | 4 | 100.0 |
| *Clostridium perfringens* (N = 21) | | | | | *Propionibacterium acnes* (N = 21) | | | | |
| Besifloxacin | 0.12-0.25 | 0.25 | 0.25 | na | Besifloxacin | 0.12-0.25 | 0.25 | 0.25 | na |
| Moxifloxacin | 0.25-0.5 | 0.5 | 0.5 | 100.0 | Moxifloxacin | 0.25-0.25 | 0.25 | 0.25 | 100.0 |
| Gatifloxacin | 0.5-1 | 1 | 1 | na | Gatifloxacin | 0.25-0.5 | 0.25 | 0.5 | na |
| Clindamycin | 0.06-4 | 2 | 4 | 85.7 | Clindamycin | ≦0.03-2 | 0.06 | 0.12 | 100.0 |
| Metronidazole | 1-4 | 2 | 4 | 100.0 | Metronidazole | >16->16 | >16 | >16 | 0.0 |
| *Fusobacterium* spp. (N = 21) | | | | | | | | | |
| Besifloxacin | 0.12-8 | 0.25 | 1 | na | | | | | |
| Moxifloxacin | 0.25->16 | 1 | 2 | 95.2 | | | | | |
| Gatifloxacin | 0.5->16 | 1 | 4 | na | | | | | |
| Clindamycin | 0.06-8 | 0.06 | 2 | 95.2 | | | | | |
| Metronidazole | ≦0.12-2 | 0.25 | 1 | 100.0 | | | | | |

[a] Percent of susceptible isolates. Clinical and Laboratory Standards Institute's breakpoints were not available for some antibacterials for the interpretation as susceptible, intermediate, or resistant.
na = Not applicable.

TABLE 8

Integrated Summary of Besifloxacin MIC Data for Pathogens Associated With Bacterial Conjunctivitis From Preclinical Studies

| Organism | No. of Studies | Total N | Besifloxacin MIC$_{50}$ (μg/mL) | Besifloxacin MIC$_{90}$ (μg/mL) | Range |
|---|---|---|---|---|---|
| Combined | | | | | |
| Key Organisms[a] | 5 | 1205 | 0.06 | 1 | ≦0.004->8 |
| Key Organisms[a] Quinolone-S[b] | 5 | 894 | 0.06 | 0.12 | ≦0.004-1 |
| Gram-positive | | | | | |
| *Corynebacterium species*[c] | 1 | 30 | 0.25 | 2 | ≦0.06-2 |
| *Staphylococcus aureus*[d] | | | | | |
| MRSA-QR | 3 | 73 | 1 | 4 | 0.25-8 |
| MRSA-QS | 3 | 36 | 0.03 | 0.06 | 0.015-0.25 |
| MSSA-QR | 2 | 12 | 0.25 | 4 | 0.03-4 |
| MSSA-QS | 3 | 80 | 0.03 | 0.06 | 0.015-0.12 |
| *Staphylococcus epidermidis*[d] | | | | | |
| MRSE-QR | 2 | 32 | 2 | 4 | 0.25-8 |
| MRSE-QS | 2 | 23 | 0.03 | 0.06 | 0.015-0.12 |
| MSSE-QR | 2 | 5 | 0.5 | — | 0.25-1 |
| MSSE-QS | 2 | 39 | 0.03 | 0.06 | 0.015-0.06 |
| *Staphylococcus hominis*[b] | | | | | |
| Quinolone-S | 1 | 15 | 0.03 | 0.06 | 0.015-0.06 |
| Quinolone-R | 1 | 35 | 0.25 | 1 | 0.125-2 |
| *Staphylococcus lugdunensis*[b] | | | | | |
| Quinolone-S | 1 | 10 | 0.03 | 0.06 | 0.015-0.06 |
| Quinolone-R | 1 | 5 | 0.5 | 2 | 0.125-2 |
| *Streptococcus mitis* group[e] | 1 | 90 | 0.06 | 0.12 | 0.015-2 |
| *Streptococcus oralis* | 1 | 22 | 0.06 | 0.12 | 0.03-2 |
| *Streptococcus pneumoniae*[b] | | | | | |
| Quinolone-R | 1 | 23 | 1 | 4 | 0.5->8 |
| Penicillin-S | 3 | 123 | 0.12 | 0.12 | 0.015-1 |
| Penicillin-I | 2 | 28 | 0.12 | 0.12 | 0.03-0.25 |
| Penicillin-R | 3 | 61 | 0.12 | 0.12 | 0.03-0.25 |
| *Streptococcus pyogenes* | 2 | 201 | 0.06 | 0.12 | 0.03-0.12 |
| *Streptococcus salivarius* | 1 | 2 | — | — | 0.06 |
| Gram-negative | | | | | |
| *Acinetobacter lwoffii* | 1 | 13 | 0.5 | 0.5 | 0.12-2 |
| *Acinetobacter baumanii*[b] | | | | | |
| Quinolone-S | 1 | 43 | 0.5 | 2 | 0.25-4 |
| Quinolone-R | 1 | 5 | >8 | — | 2->8 |
| *Acinetobacter baumannii-calcoaceticus*[b] | | | | | |
| Quinolone-S | 1 | 23 | 0.5 | 1 | 0.12-4 |
| Quinolone-R | 1 | 10 | >8 | >8 | 8->8 |
| *Citrobacter koser*[b] | | | | | |
| Quinolone-S | 1 | 99 | 0.06 | 0.25 | 0.03-4 |
| Quinolone-R | 1 | 1 | — | — | >8 |

TABLE 8-continued

Integrated Summary of Besifloxacin MIC Data for Pathogens Associated With Bacterial Conjunctivitis From Preclinical Studies

| Organism | No. of Studies | Total N | Besifloxacin MIC$_{50}$ (µg/mL) | MIC$_{90}$ (µg/mL) | Range |
|---|---|---|---|---|---|
| *Enterobacter cloacae*[b] | | | | | |
| Quinolone-S | 1 | 58 | 0.25 | 0.5 | 0.12-2 |
| Quinolone-R | 1 | 1 | — | — | >8 |
| *Enterobacter aerogene*[b] | | | | | |
| Quinolone-S | 1 | 37 | 0.25 | 2 | 0.12-4 |
| Quinolone-R | 1 | 2 | — | — | 4->8 |
| *Haemophilus influenzae* (all phenotypes) | 3 | 243 | 0.03 | 0.06 | ≦0.004-0.25 |
| β-lactamase+ | 3 | 118 | 0.03 | 0.06 | 0.008-0.12 |
| β-lactamase− | 3 | 100 | 0.03 | 0.03 | ≦0.004-0.12 |
| β-lactamase− Ampicillin-R | 1 | 25 | 0.12 | 0.25 | 0.015-0.25 |
| *Klebsiella oxytoca*[b] | | | | | |
| Quinolone-S | 1 | 45 | 0.12 | 0.5 | 0.06-1 |
| Quinolone-R | 1 | 5 | 8 | — | 1-8 |
| *Legionella pneumophila* | 1 | 50 | 0.03 | 0.03 | 0.015-0.06 |
| *Moraxella catarrhalis* | 2 | 201 | 0.06 | 0.12 | 0.015-0.12 |
| *Moraxella species*[c] | 1 | 30 | ≦0.06 | 0.13 | ≦0.06-0.13 |
| *Morganella morganii*[b] | | | | | |
| Quinolone-S | 1 | 39 | 0.12 | 1 | 0.03-2 |
| Quinolone-R | 1 | 12 | 4 | 8 | 2->8 |
| *Neisseria gonorrhoeae* | 1 | 103 | 0.015 | 0.015 | 0.004-2 |
| *Pseudomonas aeruginosa*[b] | | | | | |
| Quinolone-S | 1 | 49 | 1 | 2 | 0.5-4 |
| Quinolone-R | 1 | 51 | >8 | >8 | 2->8 |
| *Proteus mirabilis*[b] | | | | | |
| Quinolone-S | 1 | 98 | 0.5 | 1 | 0.25-4 |
| Quinolone-R | 1 | 2 | — | — | 2->8 |
| *Serratia marcescens*[b] | | | | | |
| Quinolone-S | 1 | 98 | 1 | 2 | 0.25-2 |
| Quinolone-R | 1 | 2 | — | — | 4->8 |
| Anaerobes[c] | | | | | |
| *Clostridium perfringens* | 1 | 21 | 0.25 | 0.25 | 0.12-0.25 |
| *Propionibacterium acnes* | 1 | 21 | 0.25 | 0.25 | 0.12-0.25 |
| *Bacteroides fragilis* | 1 | 20 | 0.5 | 1 | 0.25-2 |
| *Fusobacterium species* | 1 | 21 | 0.25 | 1 | 0.12-8 |
| *Prevotella species* | 1 | 20 | 1 | 4 | 0.06-16 |

MIC$_{50}$ = Minimum inhibitory concentration required to inhibit the growth of 50% of organisms; MIC$_{90}$ = Minimum inhibitory concentration required to inhibit the growth of 90% of organisms.
[a]Presented are MIC values from nonclinical studies for the following key organisms: *Staphylococcus aureus*, *Staphylococcus epidermidis*, *Staphylococcus hominis*, *Staphylococcus lugdunensis*, *Streptococcus pneumoniae*, *Streptococcus oralis*, *Streptococcus mitis* group, *Streptococcus salivarius*, *Haemophilus influenzae*, and *Moraxella catarrhalis*.
[b]In this table, CLSI breakpoints for additional fluoroquinolones were utilized to define quinolone resistant (QR) or quinolone susceptible (QS) subsets. QR subsets in this table thus include all isolates categorized as intermediate or resistant either to ciprofloxacin, gatifloxacin, levofloxacin, or ofloxacin as appropriate.
[c]MIC values were obtained by the agar dilution method.
[d]MRSA = Methicillin-resistant *S. aureus*; MSSA = Methicillin-susceptible *S. aureus*; MRSE = Methicillin-resistant *S. epidermidis*; MSSE = Methicillin-susceptible *S. epidermidis*; S = Susceptible; R = Resistant.
[e]In this analysis, *S. mitis* group includes only isolates identified as *S. mitis* or *S. mitis* group.

Comparison of Besifloxacin MIC Data from Clinical and Non-Clinical Studies

In addition to the nonclinical studies, all baseline pathogens isolated from three besifloxacin safety and efficacy clinical trials (studies 373, 433, and 434) were tested for susceptibility to various ophthalmic antibacterial agents, including besifloxacin.

Overall, isolates cultured in the three besifloxacin clinical efficacy trials yielded besifloxacin activity profiles similar to those seen in the nonclinical data. A total of 1324 isolates were recovered from patients at baseline (Visit 1) in the culture-confirmed population species-specific study eye across all treatment groups (besifloxacin ophthalmic suspension, vehicle, and Vigamox®). The MIC$_{50}$/MIC$_{90}$ values for the 1324 isolates of all species were 0.06/0.25 µg/mL for besifloxacin. Of the 1324 bacterial isolates, 886 (66.9%) were Gram-positive, while the remaining 438 (33.1%) were Gram-negative. The besifloxacin MIC$_{50}$/MIC$_{90}$ values were 0.06/0.25 µg/mL for Gram-positive bacteria and 0.03/0.5 µg/mL for Gram-negative bacteria.

When the 1324 clinical isolates were compared with 1205 nonclinical isolates of key organisms, a similar besifloxacin MIC distribution was observed. The besifloxacin MIC$_{50}$ was 0.06 µg/mL for both clinical and nonclinical isolates. Because higher proportions of quinolone-resistant strains were present in the nonclinical studies than were recovered during besifloxacin clinical trials, the overall nonclinical isolate MIC$_{90}$ value was 4-fold higher than the clinical MIC$_{90}$ value (1 and 0.25 µg/mL, respectively). However, besifloxacin MIC distributions were similar when clinical isolates were compared to only the 894 quinolone-susceptible nonclinical isolates, with equivalent MIC$_{50}$/MIC$_{90}$ values between all clinical isolates and quinolone-susceptible nonclinical isolates (0.06/0.25 and 0.06/0.12 µg/mL, respectively)

Toxicology

The non-clinical ocular tolerance of besifloxacin was shown to be acceptable with no adverse effects observed after QID dosing for 28 days. ERG measurements were included in the studies due to the known retinal toxicity associated with some fluoroquinolones.

The non-clinical systemic toxicity profile of besifloxacin was evaluated in 28-day repeat dose studies and the safety pharmacology studies showed that besifloxacin was safe. The in vivo cardiovascular effects, specifically, an increase in QT duration, following besifloxacin systemic dosing were only observed after doses that were at least 300 times the intended ocular daily dose. There was no change in heart rate, blood pressure, or cardiac conduction.

The intended dosing level in patients allowed for satisfactory safety margins, indicating an absence of any risks to humans.

In conclusion, the overall nonclinical profile obtained with besifloxacin is not unexpected, and demonstrates similarities with other fluoroquinolones. Systemic effects of besifloxacin were only observed at plasma concentrations that would not likely be achieved following ocular administration of besifloxacin ophthalmic suspension. Consequently, these effects, while in some cases consistent with the class effects observed with other fluoroquinolones, present no reasonable risk to humans following ocular use of the product.

Pharmacokinetics

Results from the nonclinical ocular pharmacokinetic (PK) studies indicate that topical ocular administration of besifloxacin ophthalmic suspension, 0.6%, is associated with rapid absorption and distribution of besifloxacin into ocular tissues. Following the initial rapid absorption into ocular tissues, besifloxacin is eliminated from these tissues with an apparent half-life of more than 5 hours. Repeated (twice daily or BID, TID, and QID) topical ocular administration of besifloxacin was associated with low systemic exposure ($C_{max}$<0.025 µg/g in non-excretory organs), while increased exposure to pigmented ocular tissues was observed following QID dosing. However, based on the extensive ocular safety data available for besifloxacin, no adverse consequences are expected.

Systemic exposure to besifloxacin following topical ocular administration was low, with peak plasma besifloxacin concentrations of 7.6 and 9.2 ng/mL, respectively, on average.

Clinical Pharmacology

Pharmacokinetics

Figure 2:
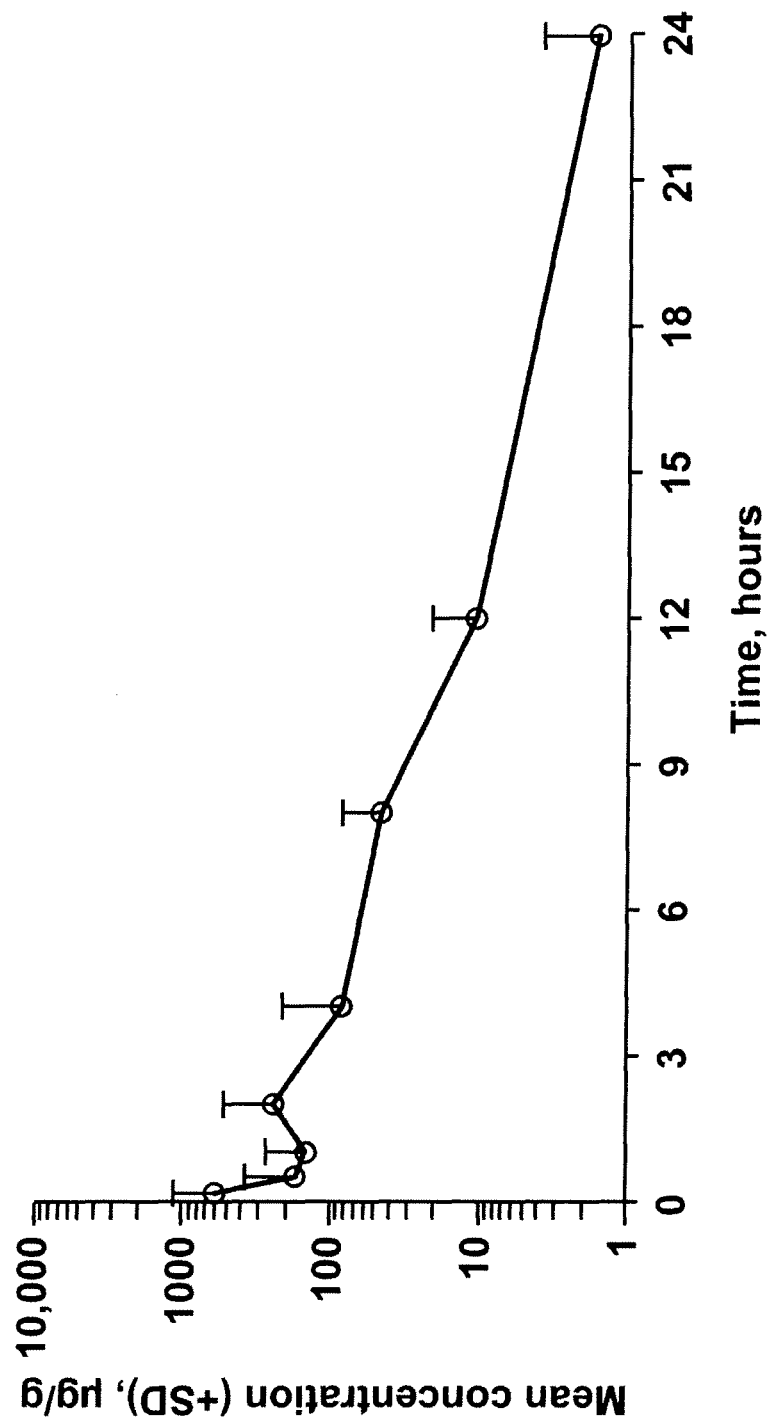
FIG. 2 shows besifloxacin concentration-time profile in tears after single administration of besifloxacin to healthy volunteers (study 424).
Figure 3:
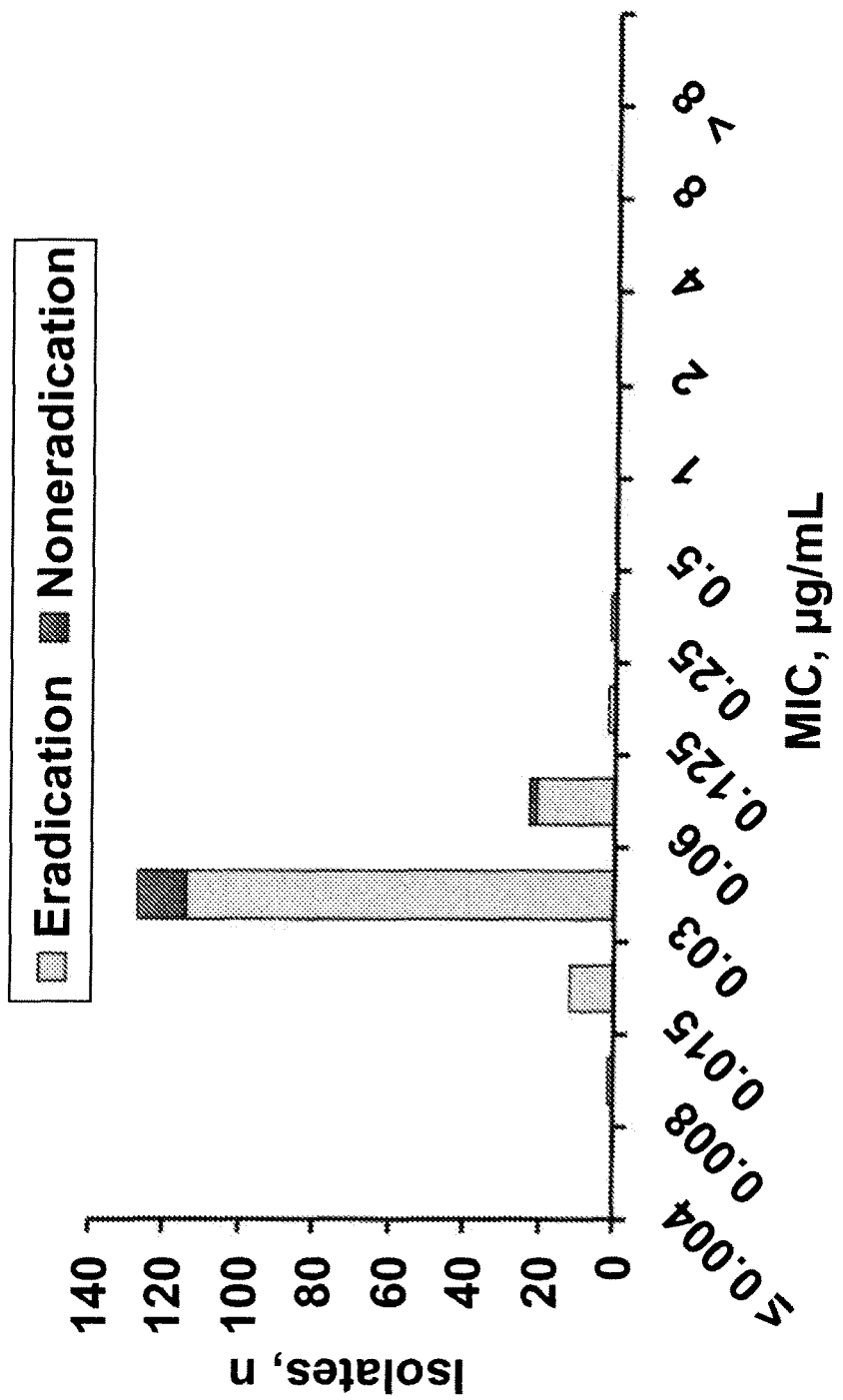
FIG. 3 shows baseline *H. influenzae* (all phenotypes) species-specific microbial eradication in study eyes in Studies 373, 433, and 434 (culture-confirmed, as treated).
Figure 4:
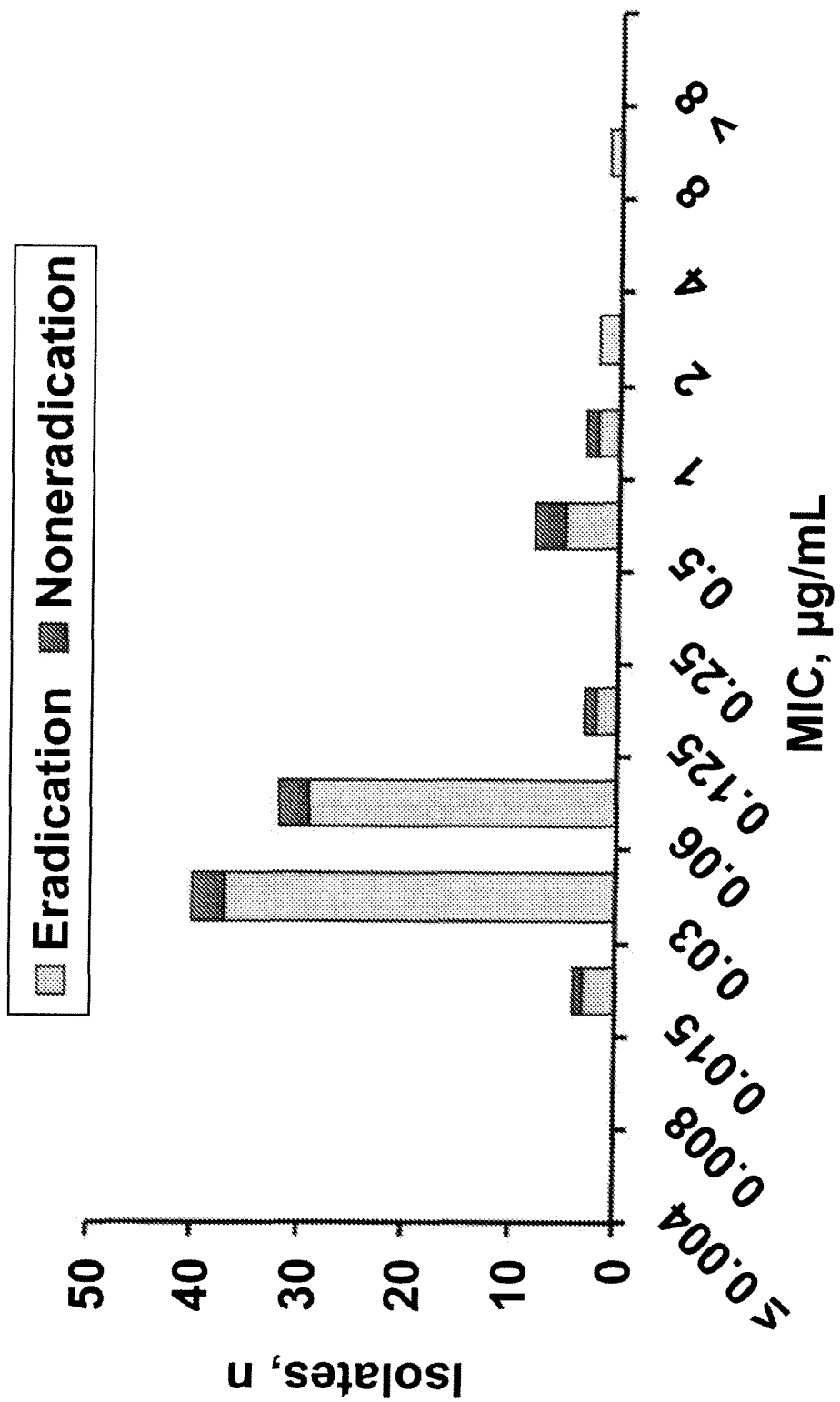
FIG. 4 shows baseline *S. aureus* (all phenotypes) species-specific microbial eradication in study eyes in Studies 373, 433, and 434 (culture-confirmed, as treated).
Figure 5:
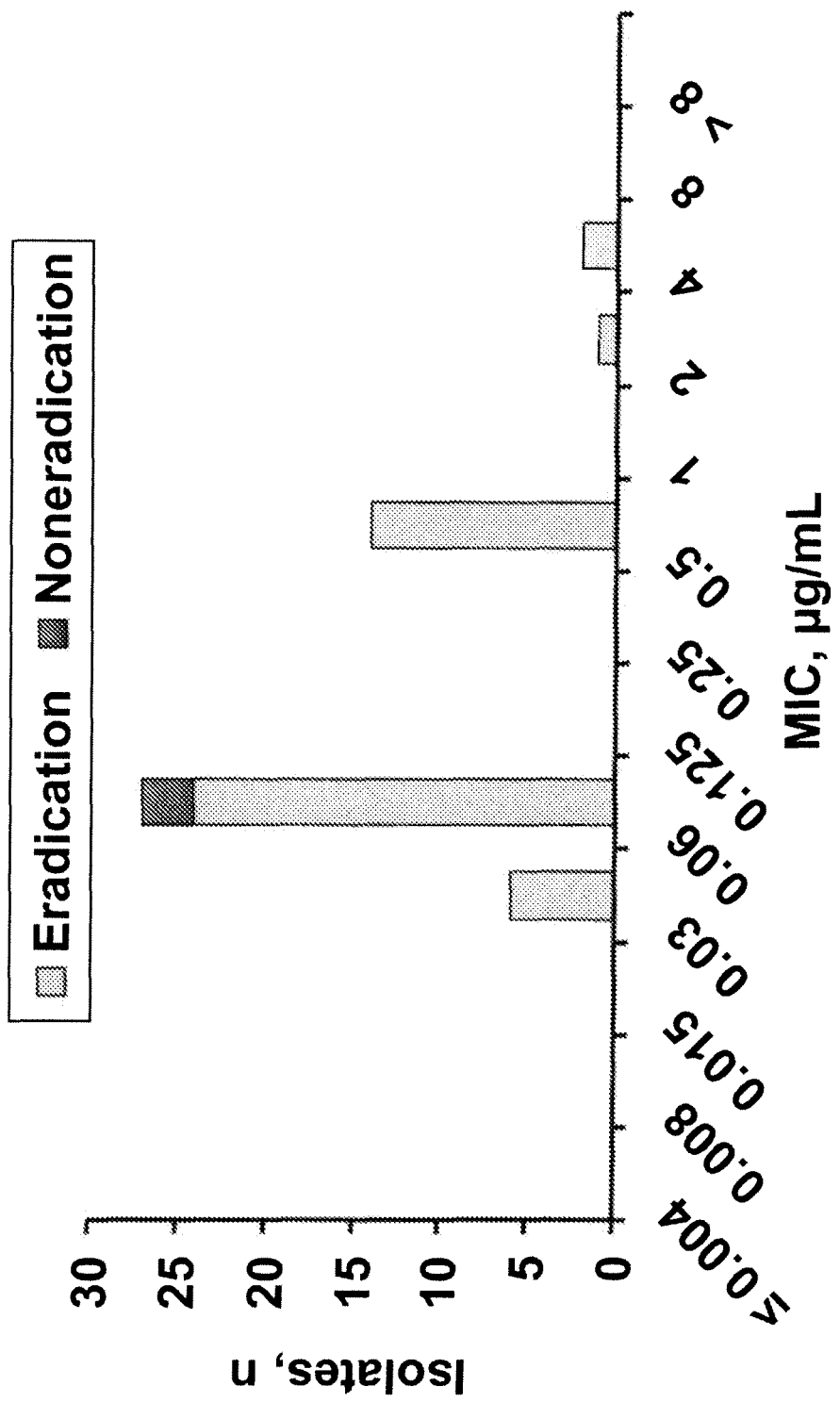
FIG. 5 shows baseline *S. epidermidis* (all phenotypes) species-specific microbial eradication in study eyes in Studies 373, 433, and 434 (culture-confirmed, "as treated").
Figure 6:
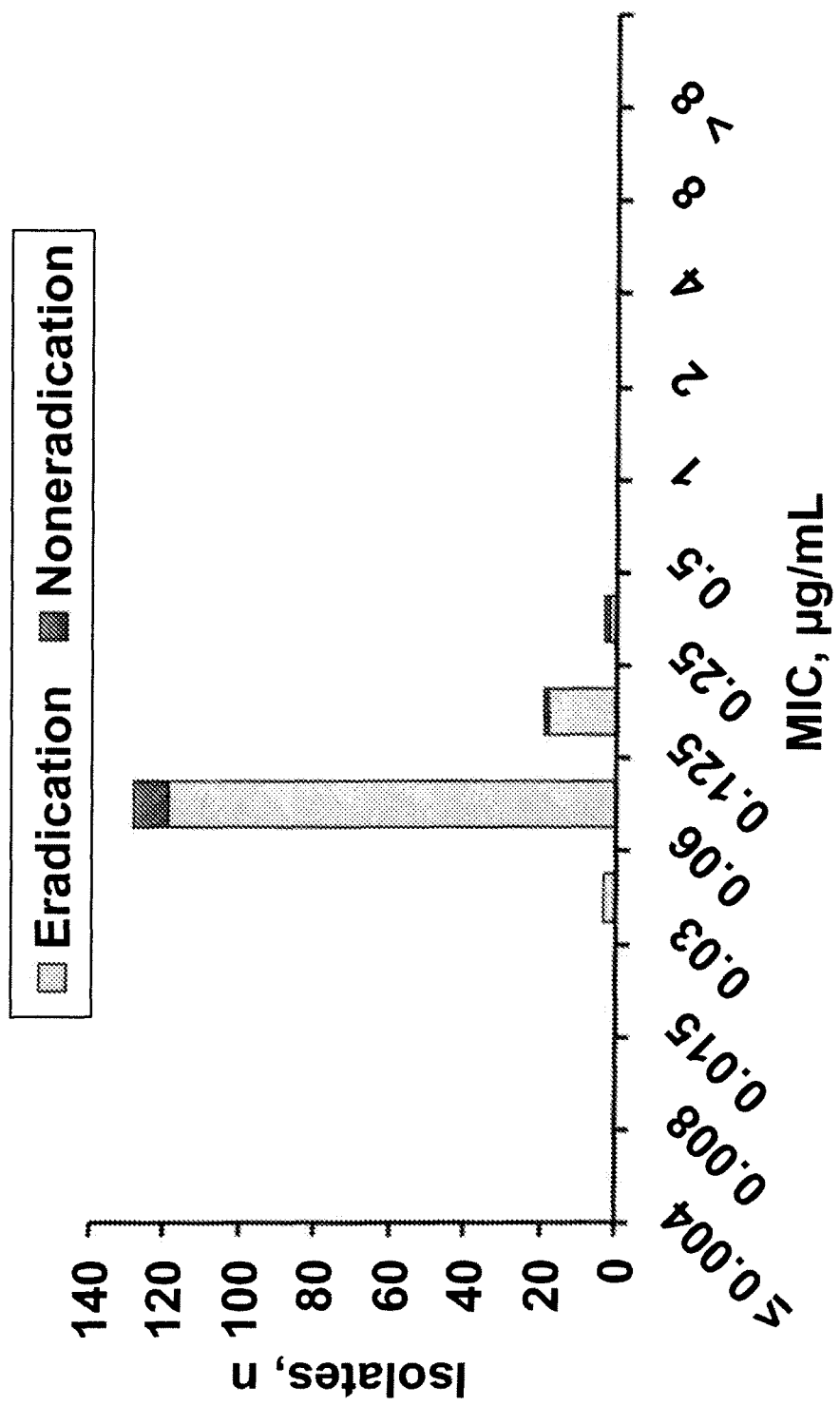
FIG. 6 shows baseline *S. pneumoniae* (all phenotypes) species-specific microbial eradication in study eyes in Studies 373, 433, and 434 (culture-confirmed, as treated).

Study 424—Ocular (Tear Fluid) Exposure to Besifloxacin Following Topical Ocular Administration in Healthy Volunteers This study was conducted to evaluate the ocular PK of besifloxacin in tear fluid after a single instillation of besifloxacin ophthalmic suspension, 0.6%, in both eyes of healthy volunteers and to compare the actual besifloxacin exposure to MICs of the most prevalent pathogens associated with bacterial conjunctivitis.

µg/g) (Table 9 and FIG. 2). Concentrations of 1.6 µg/g or higher were sustained for at least 24 hours after dosing. Based on $AUC_{0-24}$, the total exposure to besifloxacin was 1232 µg·h/g. Elimination of besifloxacin from tears occurred at an estimated half-life of 3.4 hours. Therapeutic levels of besifloxacin were achieved in tears after a single instillation, as indicated by comparing the besifloxacin tear levels to the $MIC_{90}$ values of 1 µg/mL for *S. aureus* and ≦0.06 µg/mL for *H. influenzae*. The resulting $C_{max}/MIC_{90}$ ratios (610 and ≧10167) and the $AUC_{24}/MIC_{90}$ ratios (1232 and ≧20533) based on the FAS data for *S. aureus* and *H. influenzae*, respectively, are higher than the published target values associated with bacterial eradication in plasma for fluoroquinolones.

In conclusion, topical ocular application of besifloxacin ophthalmic suspension, 0.6%, resulted in high therapeutic levels of besifloxacin in human tear samples that were sustained at a level of 1.6 µg/g or higher for at least 24 hours after a single dose. The maximum concentration of besifloxacin in tears was approximately 610-fold and 10,000-fold higher than the $MIC_{90}$ values for *S. aureus* and *H. influenzae*, which are 2 of the most prevalent causative ophthalmic pathogens in patients with bacterial conjunctivitis.

TABLE 9

PK/PD Parameter Values for Besifloxacin in Tears After Single Topical Ocular Instillation of Besifloxacin Ophthalmic Suspension in Healthy Volunteers (Study 424)

| Data Set | N | $t_{max}$ (h) | $C_{max}$ (µg/g) | $AUC_{24}$ (µg · h/g) | $t_{1/2}$ (h) | $C_{max}/MIC_{90}{}^a$ | $C_{max}/MIC_{90}{}^b$ | $AUC_{24}/MIC_{90}{}^a$ | $AUC_{24}/MIC_{90}{}^b$ |
|---|---|---|---|---|---|---|---|---|---|
| FAS | 64 | 0.17 | 610 | 1232 | 3.43 | 610 | ≧10167 | 1232 | ≧20533 |
| PP | 51 | 0.17 | 811 | 1523 | 3.51 | 811 | ≧13517 | 1523 | ≧25383 |

FAS = Full analysis set;
PP = Per protocol set.
$^a MIC_{90}$: *S. aureus* = 1 µg/mL.
$^b MIC_{90}$: *H. influenzae* ≦0.06 µg/mL.

This single-center, open-label, prospective study enrolled 64 healthy male and female volunteers with a mean age of 23.7 years (range, 18 to 39 years). Healthy volunteers received a single instillation (37 µL by pipette) of besifloxacin ophthalmic suspension, 0.6%, in the conjunctival sac of each eye. A single tear sample was collected on a Schirmer tear strip from each healthy volunteer. Separate subgroups of healthy volunteers (8 volunteers per collection time) were sampled at each of the 8 predetermined collection times over the period of 0.17 hours to 24 hours after dosing: 10 minutes after instillation; 30 minutes after instillation; and 1, 2, 4, 8, 12, and 24 hours after instillation. Samples were analyzed using a validated LC/MS/MS method, and the LLOQ was 2 ng/mL (equivalent to approximately 0.2 µg/g for a 10-mg tear sample).

Mean tear concentration data were obtained from the per protocol (PP) set and the full analysis (FAS) set. For the purpose of this study, the PP set included all healthy volunteers with the exclusion of apparent outlier values. The FAS set included all healthy volunteers who received besifloxacin, and from whom all sampling data were available (no exclusion of outlier values). The $MIC_{90}$ values used were those corresponding to the extreme values in sensitivity from the most frequently encountered bacteria in bacterial conjunctivitis: *S. aureus* (frequent bacteria in adults and elderly people), $MIC_{90}$=1 µg/mL and *H. influenzae* (frequent bacteria in children), $MIC_{90}$≦0.06 µg/mL.

Mean maximum besifloxacin concentrations in tears were observed within 10 minutes after instillation ($C_{max}$ 610±540

Pharmacokinetic/Pharmacodynamic Analyses

To evaluate the PK/pharmacodynamic (PD) relationship of besifloxacin, results from the ocular PK study in humans, Study 424 (described above), were used along with the in vitro $MIC_{90}$ values for prevalent bacterial pathogens isolated from bacterial conjunctivitis patients in besifloxacin clinical safety and efficacy studies 373, 433, and 434.

The relationship between the concentration of besifloxacin in human tear fluid and the concentration required for antimicrobial activity was quantified by calculating the ratios of $C_{max}/MIC_{90}$ and $AUC_{24}/MIC_{90}$. For the purpose of calculating these PK/PD ratios, a PK model was used to simulate besifloxacin concentrations with a TID dosing regimen. An additional consideration in this analysis is the potential role of protein binding, which could effectively lower the concentration of unbound (free) besifloxacin. The inhibitory effect of protein binding on antibacterial efficacy has been reported for β-lactams; however, there is no general consensus about the role of protein binding on the antibacterial activity of fluoroquinolones (Bergogne-Berezin, 2002; Craig & Ebert, 1989; Drusano, 1988; Merrikin et al., 1983; Turnidge, 1999; Zeitlinger et al., 2008). Based on the fact that besifloxacin is approximately 40% bound to proteins in human plasma (similar to other fluoroquinolones), and assuming a similar extent of binding to proteins in ocular tissue, the corresponding $C_{max}$ and $AUC_{24}$ values for free (unbound) besifloxacin would be approximately 60% of the values determined for total (bound and free) besifloxacin. In order to evaluate the potential theoretical maximum impact of protein binding on besifloxacin activity, $C_{max}/MIC_{90}$ and $AUC_{24}/MIC_{90}$ ratios were calculated based on the PK estimates for total (bound and free) and free (unbound) besifloxacin (Table 10).

TABLE 10

Predicted PK/PD Ratios for Besifloxacin in Tears After Repeated (TID) Topical Administration of Besifloxacin Ophthalmic Suspension in Healthy Volunteers

| Organism | $MIC_{90}$ (μg/mL) | $C_{max}/MIC_{90}$[a] Total[c] | Free[d] | $AUC_{24}/MIC_{90}$[b] Total[c] | Free[d] |
|---|---|---|---|---|---|
| Gram-positive | | | | | |
| Staphylococcus aureus (MRSA-C[R]) | 4 | 153 | 92 | 950 | 570 |
| Staphylococcus aureus (MSSA-C[R]) | 2 | 305 | 183 | 1901 | 1140 |
| Staphylococcus aureus (all phenotypes) | 0.5 | 1220 | 732 | 7602 | 4561 |
| Streptococcus pneumoniae | 0.125 | 4880 | 2928 | 30,408 | 18,245 |
| Staphylococcus epidermidis | 0.5 | 1220 | 732 | 7602 | 4561 |
| Gram-negative | | | | | |
| Haemophilus influenzae | 0.06 | 10,167 | 6100 | 63,350 | 38,010 |

[a]Calculations based on besifloxacin $C_{max}$ (observed) of 610 μg/g.
[b]Calculations based on besifloxacin $AUC_{24}$ (predicted, TID) of 3801 μg · hr/g.
[c]PK/PD ratios calculated based on total (bound and free) besifloxacin.
[d]PK/PD ratios calculated based on free besifloxacin levels, which were calculated using the measured value of besifloxacin binding to human plasma proteins (40% bound).

Topical ocular application of besifloxacin ophthalmic suspension, 0.6%, resulted in high therapeutic levels of besifloxacin in human tear samples, with concentrations at 24 hours (1.60±2.28 μg/g), which were above the $MIC_{90}$ values for prevalent ocular pathogens. Favorable ratios for effective and resistance-limiting levels of anti-infective agents have been proposed to be $C_{max}/MIC_{90}>10$ and $AUC_{24}/MIC_{90}>30$ to 50 for Gram-positive bacteria or >100 to 125 for Gram-negative bacteria (Allen et al., 2004; Hermsen et al., 2005; Metzler et al., 2004; Smith et al., 2004; Wright et al., 2000). These ratios are useful for evaluating plasma concentrations (in the instance of systemic infections), and also have been proposed for evaluating tissue concentrations in the case of local infections (Nightingale, 2005). The predicted PK/PD ratios for besifloxacin with TID dosing against prevalent pathogens associated with bacterial conjunctivitis demonstrate that the $C_{max}/MIC_{90}$ and $AUC_{24}/MIC_{90}$ are substantially above the target values published for fluoroquinolones regardless of whether total besifloxacin concentrations or only free besifloxacin concentrations are considered. Overall, these results provide a PK/PD-based rationale that is consistent with the efficacy observed with besifloxacin in the treatment of bacterial conjunctivitis.

Summary of Clinical Pharmacology

Topical ophthalmic use of besifloxacin is not expected to elicit any systemic effects. This is based on the fact that besifloxacin ophthalmic suspension is administered locally to the eye, and that the resulting systemic exposure to besifloxacin is minimal ($C_{max}$ ~0.4 ng/mL, on average) following topical administration to humans.

Clinical and Microbial Efficacy of Besifloxacin
Background and Overview

Three independent, randomized, doubled-masked, multicenter, parallel-group, controlled studies (Studies 373, 433, and 434) were conducted to assess the safety and efficacy of besifloxacin ophthalmic suspension versus vehicle (Studies 373 and 433) or Vigamox (Study 434), administered TID (at approximately 6-hour intervals) for 5 days, in patients with bacterial conjunctivitis. The overall designs and plans of the 3 clinical studies are described below.

Study Design and Methods
Study Population

Adults and children, 1 year of age or older, were eligible for entry into the studies if they had a clinical diagnosis (via biomicroscopy) of bacterial conjunctivitis in at least 1 eye. In all 3 studies, a minimum grade 1 for ocular discharge (crusty or sticky eyelids) was required. In Study 373, a minimum grade 1 for either bulbar or palpebral conjunctival injection was required, whereas for Studies 433 and 434, a minimum of grade 1 for bulbar conjunctival injection was required. In all studies, prospective patients were required to have a pinhole visual acuity (VA)≧20/200 in both eyes, determined by age-appropriate methods. Females of childbearing potential had to use a reliable means of contraception and have a negative pregnancy test at the baseline visit. Prospective patients were excluded if they had a known hypersensitivity to fluoroquinolones or besifloxacin or any of the ingredients in the study medications, had used topical ophthalmic anti-inflammatory agents within 48 hours before and during the study, used any antibiotic within 72 hours of study entry, had suspected viral or allergic conjunctivitis or suspected iritis, or a history of recurrent corneal erosion syndrome or any active ulcerative keratitis.

Study Endpoints

The efficacy endpoints of the 3 clinical studies are summarized in Table 11. The primary efficacy endpoints were clinical resolution and microbial eradication of baseline bacterial infection at Visit 3 (Day 8 or 9) in Study 373 or Visit 2 (Day 5±1) in Studies 433 and 434. Secondary efficacy endpoints were clinical resolution and microbial eradication at Visit 2 (Day 4±1) in Study 373 or Visit 3 (Day 8 or 9) in Studies 433 and 434.

TABLE 11

Efficacy Endpoints of Studies 373, 433, and 434

| | Endpoints, study visit (day) | | |
|---|---|---|---|
| Endpoints | Study 373 | Study 433 | Study 434 |
| Primary | | | |
| Clinical resolution and microbial eradication | 3 (8 or 9) | 2 (5 ± 1) | 2 (5 ± 1) |
| Secondary | | | |
| Clinical resolution and microbial eradication | 2 (4 ± 1) | 3 (8 or 9) | 3 (8 or 9) |

Study Endpoint Definitions

Clinical resolution was defined as absence of 3 clinical signs (conjunctival discharge, bulbar and palpebral conjunctival injection) in Study 373 and 2 clinical signs (conjunctival discharge and bulbar conjunctival injection) in Studies 433 and 434. Grading scales for these clinical signs are shown in Table 12.

TABLE 12

Grading Scales for Ocular Discharge, Bulbar Conjunctival Injection and Palpebral Conjunctival Injection

| Grade | Name | Criteria |
|---|---|---|
| | | Ocular Discharge |
| 0 | Absent | No signs of discharge in conjunctiva. |
| 1 | Mild | Small amount of mucopurulent or purulent discharge noted in the lower cul-de-sac. No true matting of the eyelids in the mornings upon awakening. |
| 2 | Moderate | Moderate amount of mucopurulent or purulent discharge is noted in the lower cul-de-sac. Frank matting together of the eyelids in the morning upon awakening. |
| 3 | Severe | Profuse amount of mucopurulent or purulent discharge is noted in the lower cul-de-sac and in the marginal tear strip. Eyelids tightly matted together in the morning upon awakening, requiring warm soaks to pry the lids apart. |
| | | Bulbar Conjunctival Injection[a] |
| 0 | Normal | Normal vascular pattern. |
| 1 | Trace | Awareness eye is slightly pink in any one quadrant. |
| 2 | Moderate | Diffuse pink color in at least 3 quadrants. |
| 3 | Severe | Vasodilation in at least 3 quadrants, reddish hue. |
| | | Palpebral Conjunctival Injection[b] |
| 0 | Normal | Normal vascular pattern. |
| 1 | Trace | Trace hyperemia. |
| 2 | Moderate | Moderate hyperemia or definable papillary reaction. |
| 3 | Severe | Diffuse vasodilation. |

[a]Bulbar conjunctival injection was assessed by evaluating 4 quadrants (inferior, superior, temporal, and nasal) per grading scale provided to each clinical investigator.
[b]Palpebral conjunctival injection was only assessed as a primary endpoint in Study 373.

In all 3 studies, microbial eradication was defined as the absence of all accepted ocular bacterial species that were present at or above threshold levels at baseline.

To be considered culture-confirmed bacterial conjunctivitis, a patient had to have bacterial species identified in ocular cultures obtained at baseline from a list of accepted ocular bacterial species and corresponding colony forming unit (CFU)/mL threshold levels as defined by Leibowitz in 1991 and referred to as bacterial threshold criteria ("Cagle list") (Leibowitz, 1991). According to these criteria, an ocular specimen is considered "culture confirmed" or "culture positive" if the CFU count equals or exceeds the threshold values given for any of the following groups of organisms in Table 13. Using current bacterial nomenclature standards, study personnel at the central laboratory assigned bacterial species identified in culture obtained from patients in the 3 studies to the appropriate Cagle group for evaluation of pathogenic threshold levels. Based on current international standards for bacterial nomenclature, sponsor personnel confirmed that each pathogenic species and associated CFU/mL, threshold level was assigned to the microbiologically appropriate corresponding pathogen group defined in the Cagle list.

TABLE 13

Bacterial Threshold Criteria ("Cagle List")

| Group | Threshold (CFU/mL) | Bacterial Species |
|---|---|---|
| I | 1 | Acinetobacter sp., Achromobacter sp., Citrobacter sp., Enterobacter sp., other Enterobacteriaceae, Escherichia sp., Haemophilus sp., Klebsiella sp., Moraxella sp. (other than M. catarrhalis), Neisseria sp., Proteus/Morganella sp., Pseudomonas sp., Serratia marcescens, Streptococcus pyogenes, Streptococcus pneumoniae |
| II | 10 | Moraxella catarrhalis, Staphylococcus aureus, Group B, C, D, G, and viridians streptococci |
| III | 100 | Bacillus sp., Micrococcus sp., Staphylococcus epidermidis, other coagulase-negative Staphylococcus sp. |
| IV | 1000 | Corynebacterium sp. |

CFU = Colony forming unit.

Microbial Culture Methods
Test Method for Study 373

Microbial cultures were taken from the conjunctival cul-de-sac on each Visit prior to the administration of the morning dose. All specimens were shipped to the laboratory for analysis. Culture tests for bacteria, yeast, and virus were performed by Covance using test methods detailed in Standard Operating Procedures. Quantitative plate counts were performed on bacteria and yeast test specimens. Viral test specimens were evaluated for the presence of adenovirus, herpes simplex virus, varicella zoster virus, and enterovirus.

Representative bacterial and yeast colony types were chosen from the quantitative ocular specimen plates based on similar colony morphology and were identified. The laboratory study personnel assigned bacterial species identified in this study to the appropriate Cagle group listed in Table 15 above for evaluation of pathogenic threshold levels. If the isolate met the bacterial threshold criteria, MIC testing was performed for besifloxacin and comparator test agents following CLSI document M7-A6 (2003) "Methods for Dilution Antimicrobial Susceptibility Tests for Bacteria that Grow Aerobically." MIC test drug concentration ranges included 0.004 to 8 μg/mL for besifloxacin, azithromycin, ciprofloxacin, gatifloxacin, levofloxacin, moxifloxacin, and ofloxacin; 0.06 to 2 μg/mL for penicillin, and 0.12 to 4 μg/mL for oxacillin. CLSI document M100-S14 (2004) "Performance Standards for Antimicrobial Susceptibility Testing" was used to determine the MIC (μg/mL) Interpretive Standards for the comparator drugs. The laboratory's MIC test QC measures were performed according to CLSI documents (M7-A6, January 2003) relating to 30-day QC validations, weekly QC, and daily QC. The CLSI defined QC ranges for antimicrobials that were available for the selected American Type Culture Collection (ATCC) bacterial strains (M100-S14, 2004) were used to monitor the proper performance of the antimicrobial susceptibility test for comparator test agents. Pulsed Field Gel Electrophoresis (PFGE) was used for strain typing of bacteria with the same species recovered at or above threshold from the first and subsequent patient visits. PFGE testing was performed per standard procedures. Bacteria recovered as pathogens were stored in duplicate.

Test method for Studies 433 and 434 were identical to the ones described above with two exceptions:
 1. MIC test drug concentration ranges were 0.015 to 8 μg/mL for penicillin, and 0.03 to 8 μg/mL for oxacillin.
 2. The CLSI-defined QC ranges for antimicrobials that were available for the selected ATCC bacterial strains (M100-S16, 2006) were used to monitor the proper performance of the antimicrobial susceptibility test for comparator test agents. MIC values obtained during study 373 were used to calculate tentative besifloxacin QC ranges used for studies 433 and 434.

Analysis Populations

For presentation of the clinical efficacy analyses, patients were analyzed as randomized in the vehicle-controlled Studies 373 and 433 and as treated in the active-controlled Study 434. For the species-specific microbial eradication, baseline pathogens with levels at or above threshold were analyzed as treated.

In the 3 clinical studies, the primary efficacy analyses were performed on the intent-to-treat (ITT; Study 373) or modified intent-to-treat (mITT; Studies 433 and 434) culture-confirmed populations, defined as eyes of patients with a clinical diagnosis of bacterial conjunctivitis who received at least 1 drop of study medication and had baseline culture results indicating bacterial levels at or above threshold for any accepted ocular species defined in the protocol.

Definitions of analysis populations used in Studies 373, 433, and 434 are summarized in Table 14.

TABLE 14

Definitions of Analysis Populations

| Study Number | ITT | mITT | PP | Safety |
|---|---|---|---|---|
| Study 373 | Culture confirmed[a] | — | Culture confirmed without major protocol deviation[b] | Received ≧1 dose of study drug |
| Study 433 | Clinically diagnosed | Culture confirmed | Culture confirmed without major protocol deviation[b] | Received ≧1 dose of study drug |
| Study 434 | Clinically diagnosed | Culture confirmed | Culture confirmed without major protocol deviation[b] | Received ≧1 dose of study drug |

ITT = Intent-to-treat;
mITT = Modified intent-to-treat;
PP = Per protocol.
[a]Used for mITT integrated analysis.
[b]Discontinuations also excluded.

Designation of Study Eyes and Species-Specific Study Eyes

Each randomized patient had a single eye represented in the study eye analyses of all non-species-specific endpoints. For analyses by individual microbial species, a species-specific study eye was defined that could be different from the baseline-designated study eye defined above. The key criteria used to designate study eyes and species-specific study eyes are summarized below:

At baseline (Visit 1), patients included in the mITT and PP populations had at least one eye that (i) met clinical criteria for acute conjunctivitis, (ii) was treated with besifloxacin or control, and (iii) yielded bacterial cultures at or above defined threshold levels for that pathogen.

If only one eye met criteria (i)-(iii), then this eye was designated as the study eye. The terms baseline-designated study eye and study eye are used interchangeably.

If both eyes met criteria (i)-(iii), then the eye with the highest clinical score was designated as the study eye. If both eyes met criteria (i)-(iii) with the same clinical score, then the right eye was designated as the study eye. The eye that was not the study eye was designated as the fellow eye.

In all cases, any baseline (Visit 1) bacterial species isolated at or above threshold from an individual study eye was used in any species-specific study eye tabulations for that species.

If both patient eyes met criteria (i)-(iii), and the baseline-designated fellow eye yielded baseline cultures at or above threshold for an additional species not present at or above threshold in the study eye, then the additional bacterial species isolated at or above threshold from that patient's fellow eye was also included in tabulations of species-specific study eyes for that species.

Note that all tabulations of baseline bacterial pathogens using the species-specific study eye designation thus included isolates from a patient's fellow eye only if that species was not present at or above threshold in that patient's study eye. Therefore, the species-specific study eye designation ensured that each bacterial species was counted only once per patient in any tables or summaries presenting an analysis by species.

In summary, the study eye and fellow eye designations were used to evaluate data at the eye level, whereas the species-specific study eye and species-specific fellow eye designations were used to evaluate microbial data at the species level.

Results from Individual Studies

This section summarizes the results from the 3 independent safety and efficacy trials (Studies 373, 433, and 434) conducted with besifloxacin ophthalmic suspension in patients with bacterial conjunctivitis.

The primary efficacy endpoints were clinical resolution and microbial eradication at Visit 3 (Day 8 or 9) for Study 373 and Visit 2 (Day 5±1) for Studies 433 and 434. Clinical resolution in Study 373 was defined as absence of the following 3 clinical signs/indices: conjunctival discharge, bulbar conjunctival injection, and palpebral conjunctival injection. Clinical resolution in Studies 433 and 434 was defined as the absence of conjunctival discharge and bulbar conjunctival injection. In all studies, microbial eradication was defined as the absence of all accepted ocular bacterial species that were present at or above threshold levels at baseline.

To appropriately compare results from Studies 373, 433, and 434, additional analyses were conducted on Study 373 data for clinical resolution and microbial eradication using a definition for clinically diagnosed bacterial conjunctivitis (baseline-designated study eye) comparable to that used in Studies 433 and 434. For these additional analyses, the definition of baseline-designated study eye and analyses of clinical resolution are based on 2 clinical signs (conjunctival discharge and bulbar conjunctival injection, as used in Studies 433 and 434), whereas the original definition of study eye and analyses for Study 373 are based on 3 clinical signs (conjunctival discharge, bulbar conjunctival injection, and palpebral conjunctival injection).

Study 373
Results
Incidence of Baseline Pathogens

The range of baseline pathogens that were encountered in Study 373 is shown in Table 15. The majority of isolates consisted of *Haemophilus* spp., streptococci, staphylococci, and coryneform bacteria. These organisms are fairly common to what would be expected in any study of bacterial conjunctivitis.

TABLE 15

Baseline Pathogens With Incidence ≧1% in Species-Specific Study Eyes Across All Treatment Groups-Study 373
Besifloxacin vs Vehicle

| Organism | Incidence,[a] n (%) |
|---|---|
| H. influenzae | 46 (31.7) |
| S. pneumoniae | 40 (27.6) |
| S. aureus | 20 (13.8) |

TABLE 15-continued

Baseline Pathogens With Incidence ≧1% in Species-Specific
Study Eyes Across All Treatment Groups-Study 373
Besifloxacin vs Vehicle

| Organism | Incidence,[a] n (%) |
|---|---|
| S. epidermidis | 7 (4.8) |
| S. oralis | 4 (2.8) |
| S. mitis group[b] | 3 (2.1) |
| CDC coryneform group G | 2 (1.4) |
| Serratia marcescens | 2 (1.4) |
| Stenotrophomonas maltophilia | 2 (1.4) |
| Hoemophilus parainfluenzae | 2 (1.4) |

[a]Among 145 species-specific study eye pathogens at baseline (Visit 1).
[b]In this analysis, S. mitis group includes only isolates identified as S. mitis or S. mitis group.

Clinical Resolution

Results for clinical resolution (based on the absence of 2 and 3 clinical signs/indices) at Visit 2 (Day 4±1) and Visit 3 (Day 8 or 9) are summarized in Table 19 for the ITT, culture-confirmed population.

At Visit 3 (primary efficacy endpoint), when the last non-missing observation from Visit 2 or later was carried forward, a statistically significantly greater percentage of patients in the besifloxacin ophthalmic suspension treatment group versus vehicle treatment group experienced clinical resolution (based on absence of 3 clinical signs—conjunctival discharge, bulbar conjunctival injection, and palpebral conjunctival injection) (61.7% vs 35.7%; p=0.0013, Cochran-Mantel-Haenszel [CMH] adjusted for center effects). In addition, to better compare these results to Studies 433 and 434 and data from other recent fluoroquinolone development programs, clinical resolution in the baseline-designated study eye was analyzed based on the absence of 2 clinical signs (conjunctival discharge and bulbar conjunctival injection). When missing values and discontinued patients were imputed as clinical resolution failures, a statistically significant greater rate of clinical resolution was observed in the besifloxacin ophthalmic suspension treatment group versus vehicle treatment group at Visit 3 (73.3% vs 43.1%; p=0.0014, exact Pearson chi-squared test value not adjusted for center effects, or p=0.0004, CMH adjusted for center effects).

For the secondary efficacy endpoint, clinical resolution at Visit 2 (Day 4±1), no statistically significant difference was observed between the besifloxacin ophthalmic suspension treatment group versus vehicle treatment group based on an analysis of the absence of 3 clinical signs (Table 16) or 2 clinical signs (Table 16).

TABLE 16

Clinical Resolution by 2 or 3 Indices at Visit 2 (Day 4 ± 1) and
Visit 3 (Day 8 or 9) (ITT, Culture Confirmed)-Study 373

| | Visit 2 (Day 4 ± 1) | | Primary Endpoint Visit 3 (Day 8 or 9) | |
|---|---|---|---|---|
| Clinical Resolution (3 indices)[a] | Besifloxacin (N = 60) | Vehicle (N = 56) | Besifloxacin (N = 60) | Vehicle (N = 56) |
| Yes, n (%) | 14 (23.3) | 8 (14.3) | 37 (61.7) | 20 (35.7) |
| No, n (%) | 46 (76.7) | 48 (85.7) | 23 (38.3) | 36 (64.3) |
| p value[c] | 0.2434/0.3144 | | 0.0058/0.0013 | |
| Clinical Resolution (2 indices)[b] | Besifloxacin (N = 60) | Vehicle (N = 58) | Besifloxacin (N = 60) | Vehicle (N = 58) |
| Resolution, n (%) | 20 (33.3) | 10 (17.2) | 44 (73.3) | 25 (43.1) |
| Non-resolution,[d] n (%) | 40 (66.7) | 48 (82.8) | 16 (26.7) | 33 (56.9) |

TABLE 16-continued

Clinical Resolution by 2 or 3 Indices at Visit 2 (Day 4 ± 1) and
Visit 3 (Day 8 or 9) (ITT, Culture Confirmed)-Study 373

| p value[c] | 0.0574/0.0691 | 0.0014/0.0004 |
|---|---|---|
| 95% CI[e] | (0.21, 31.97) | (12.26, 48.20) |

CI = Confidence interval.
[a]Clinical resolution defined as the absence of ocular discharge, bulbar conjunctival injection, and palpebral conjunctival injection, based on the original analyses.
[b]Clinical resolution defined as the absence of ocular discharge and bulbar conjunctival injection, based on the additional analyses.
[c]p values from exact Pearson chi-squared test/CMH test stratified by center, respectively.
[d]Non-resolution refers to any score other than 'resolution.' Missing or discontinued patients imputed as 'non-resolution.'
[e]Difference calculated as besifloxacin minus vehicle. Positive values favor besifloxacin.

Microbial Eradication

Results for microbial eradication at the eye level (eradication of all baseline pathogens) at Visit 2 (Day 4±1) and Visit 3 (Day 8 or 9) are summarized for the ITT, culture-confirmed population in Table 20 and illustrated in FIG. 9. At Visit 3 (primary efficacy endpoint), when the last non-missing post-baseline observation was carried forward, a statistically significant greater percentage of patients in the besifloxacin ophthalmic suspension treatment group versus vehicle treatment group experienced microbial eradication (90.0% vs 69.1%; p=0.0092, exact Pearson chi-squared test; p=0.0041, CMH adjusted for center effects). For the secondary efficacy endpoint, microbial eradication at Visit 2 (Day 4±1), a significantly greater rate of microbial eradication was observed in the besifloxacin ophthalmic suspension treatment group versus vehicle treatment group (90.0% vs 51.8%; p<0.0001, exact Pearson chi-squared test; p<0.0001, CMH adjusted for center effects) (Table 17).

TABLE 17

Microbial Eradication at Visit 2 (Day 4 ± 1) and
Visit 3 (Day 8 or 9) (ITT, Culture Confirmed)-Study 373

| | Visit 2 (Day 4 ± 1) | | Primary Endpoint Visit 3 (Day 8 or 9) | |
|---|---|---|---|---|
| Microbial Eradication | Besifloxacin (N = 60) | Vehicle (N = 54) | Besifloxacin (N = 60) | Vehicle (N = 55) |
| Yes, n (%) | 54 (90.0) | 28 (51.8) | 54 (90.0) | 38 (69.1) |
| No, n (%) | 6 (10.0) | 26 (48.1) | 6 (10.0) | 17 (30.9) |
| p value[a] | <0.0001/<0.0001 | | 0.0092/0.0041 | |

CI = Confidence interval.
[a]p values from exact Pearson chi-squared test/CMH test stratified by center, respectively.
Note:
Depending on the number of bacterial species at or above threshold at Day 1, each patient may present multiple scores.

Microbial Eradication of Baseline Pathogens

Microbial eradication at Visit 3 (Day 8 or 9) by baseline pathogens is shown in Table 18 for besifloxacin versus vehicle. The species-specific eradication data show the broad-spectrum nature of besifloxacin and the high rates of eradication regardless of the Gram-stain characteristics of the organisms.

TABLE 18

Microbial Eradication at Visit 3 (Day 8 or 9) by Baseline Species-Specific Study Eye Isolates With Incidence ≧1% in Study 373-Besifloxacin vs Vehicle

| Pathogen | Isolates eradicated/encountered (%) | |
|---|---|---|
|  | Besifloxacin | Vehicle |
| Gram-positive isolates | 41/47 (87) | 22/40 (55) |
| Gram-negative isolates | 28/29 (97) | 22/29 (76) |
| H. influenzae | 24/25 (96) | 17/21 (81) |
| S. aureus | 9/10 (90) | 4/10 (40) |
| S. epidermidis | 3/3 (100) | 1/4 (25) |
| S. pneumoniae | 19/24 (79) | 8/16 (50) |
| S. oralis | 2/2 (100) | 2/2 (100) |
| CDC coryneform group G | 2/2 (100) | 0 |

Lack of Fluoroquinolone Resistance Development During Study 373

A total of 47 pathogens isolated at or above threshold at Visit 2 or Visit 3 (11 besifloxacin treated, 36 vehicle treated) were determined by PFGE analysis to be genetically concordant. MIC testing of all 47 genetically concordant isolate pairs indicated that susceptibility of Visit 2 or Visit 3 isolates did not increase by more than 2-fold for any of the tested fluoroquinolones, including besifloxacin.

Efficacy Conclusions for Study 373

In patients with culture-confirmed bacterial conjunctivitis, the primary efficacy endpoints of clinical resolution and bacterial eradication at Visit 3 (Day 8 or 9) were achieved in a significantly greater percentage of patients who received besifloxacin ophthalmic suspension versus vehicle. These findings were observed based on both the original analysis with clinical resolution defined as the absence of 3 clinical signs (conjunctival discharge, bulbar and palpebral conjunctival injection) and the additional analysis with clinical resolution defined as the absence of 2 clinical signs (conjunctival discharge and bulbar conjunctival injection). Furthermore, besifloxacin showed potent antimicrobial activity against a wide range of organisms.

Study 433

Results

Incidence of Baseline Pathogens

Comparable to Study 373, a wide range of baseline pathogens were encountered in Study 433. S. pneumoniae, H. influenzae, S. aureus, and S. epidermidis were observed most frequently in this and other studies, and these formed the primary basis of the microbiological analysis of the organisms encountered (Table 19).

TABLE 19

Baseline Pathogens With Incidence ≧1% in Species-Specific Study Eyes Across All Treatment Group-Study 433 Besifloxacin vs Vehicle

| Organism | Incidence,[a] (%) |
|---|---|
| S. pneumoniae | 140 (29.2) |
| H. influenzae | 129 (26.9) |
| S. aureus | 55 (11.5) |
| S. epidermidis | 34 (7.1) |
| S. mitis group[b] | 29 (6.0) |
| CDC coryneform group G | 9 (1.9) |

TABLE 19-continued

Baseline Pathogens With Incidence ≧1% in Species-Specific Study Eyes Across All Treatment Group-Study 433 Besifloxacin vs Vehicle

| Organism | Incidence,[a] (%) |
|---|---|
| Brevibacterium spp.[c] | 6 (1.2) |
| Streptococcus spp.[c] | 6 (1.2) |
| S. salivarius | 5 (1.0) |

[a] Among 480 species-specific study eye pathogens at baseline (Visit 1).
[b] In this analysis, S. mitis group includes only isolates identified as S. mitis or S. mitis group.
[c] Species name could not be determined.

Clinical Resolution

Results for clinical resolution by 2 clinical signs/indices (conjunctival discharge and bulbar conjunctival injection) at Visit 2 (Day 5±1) and Visit 3 (Day 8 or 9) are summarized in Table 20 for the mITT, culture-confirmed, as-randomized population. At Visit 2 (primary efficacy endpoint), when missing values and discontinued patients were imputed as clinical resolution failures, a statistically significantly greater percentage of patients in the besifloxacin ophthalmic suspension treatment group versus vehicle treatment group had clinical resolution (45.2% vs 33.0%; p=0.0169, exact Pearson chi-squared test value not adjusted for center effects or p=0.0084, CMH adjusted for center effects).

At Visit 3, when missing values and discontinued patients were imputed as clinical resolution failures, a statistically significantly greater percentage of patients in the besifloxacin ophthalmic suspension treatment group versus vehicle treatment group experienced clinical resolution (84.4% vs 69.1%; p=0.0005, exact Pearson chi-squared test value not adjusted for center effects or p=0.0011, CMH adjusted for center effects).

TABLE 20

Clinical Resolution by 2 Indices at Visit 2 (Day 5 ± 1) and Visit 3 (Day 8 or 9) (mITT, Culture Confirmed, As Randomized)-Study 433

| Clinical Resolution (2 indices)[a] | Primary Endpoint Visit 2 (Day 5 ± 1) | | Visit 3 (Day 8 or 9) | |
|---|---|---|---|---|
|  | Besifloxacin (N = 199) | Vehicle (N = 191) | Besifloxacin (N = 199) | Vehicle (N = 191) |
| Yes, n (%) | 90 (45.2) | 63 (33.0) | 168 (84.4) | 132 (69.1) |
| No, n (%) | 109 (54.8) | 128 (67.0) | 31 (15.6) | 59 (30.9) |
| p value[b] | 0.0169/0.0084 | | 0.0005/0.0011 | |
| 95% CI[c] | (2.52, 21.97) | | (6.92, 23.70) | |

CI = Confidence interval.
[a] Ocular discharge and bulbar conjunctival injection.
[b] p values from exact Pearson chi-squared test/CMH test stratified by center, respectively.
[c] Difference calculated as besifloxacin minus vehicle. Positive values favor besifloxacin.

Microbial Eradication

Results for eradication of baseline bacterial infection at Visit 2 (Day 5±1) and Visit 3 (Day 8 or 9) are summarized in Table 21. At Visit 2 (primary efficacy endpoint), when missing values and discontinued patients were imputed as microbial eradication failures, the percentage of patients in the besifloxacin ophthalmic suspension treatment group who had microbial eradication was statistically significantly greater compared with the vehicle treatment group (91.5% vs 59.7%; p<0.0001, exact Pearson chi-squared test value not adjusted for center effects or CMH adjusted for center effects). This benefit of besifloxacin ophthalmic suspension over vehicle in eradicating baseline bacterial infection was maintained at Visit 3 (88.4% vs 71.7%; p<0.0001, exact Pearson chi-squared test value not adjusted for center effects or CMH adjusted for center effects).

TABLE 21

Microbial Eradication at Visit 2 (Day 5 ± 1) and Visit 3 (Day 8 or 9) (mITT, Culture-confirmed, As Randomized)-Study 433

| Microbial Eradication (missing or discontinued patients imputed as 'no') | Primary Endpoint Visit 2 (Day 5 ± 1) | | Visit 3 (Day 8 or 9) | |
|---|---|---|---|---|
| | Besifloxacin (N = 199) | Vehicle (N = 191) | Besifloxacin (N = 199) | Vehicle (N = 191) |
| Yes, n (%) | 182 (91.5) | 114 (59.7) | 176 (88.4) | 137 (71.7) |
| No, n (%) | 17 (8.5) | 77 (40.3) | 23 (11.6) | 54 (28.3) |
| p value[a] | <0.0001/<0.0001 | | <0.0001/<0.0001 | |
| 95% CI[b] | (23.25, 40.29) | | (8.79, 24.64) | |

CI = Confidence interval;
CMH = Cochran-Mantel-Haenszel.
[a]p values from exact Pearson chi-squared test/CMH test stratified by center, respectively.
[b]Difference calculated as besifloxacin minus vehicle. Positive values favor besifloxacin.

Microbial Eradication of Baseline Pathogens

Microbial eradication at Visit 3 (Day 8 or 9) is shown by baseline pathogens in Table 22 for besifloxacin versus vehicle. Comparable to Study 373, these results show a broad-spectrum nature of the microbial eradication with besifloxacin, very high eradication rates independent of the Gram-stain characteristics, and high eradication rates for the most prevalent organisms encountered.

TABLE 22

Microbial Eradication at Visit 2 (Day 5 ± 1) by Baseline Species-Specific Study Eye Isolates With Incidence ≧1% in Study 433-Besifloxacin vs Vehicle

| | Isolates eradicated/ encountered (%) | |
|---|---|---|
| Pathogen | Besifloxacin | Vehicle |
| Gram-positive isolates | 159/173 (92) | 97/155 (63) |
| Gram-negative isolates | 69/78 (89) | 50/74 (68) |
| H. influenzae | 55/63 (87) | 43/66 (65) |
| S. aureus | 23/24 (96) | 13/31 (42) |
| S. epidermidis | 17/18 (94) | 11/16 (69) |
| S. pneumoniae | 66/73 (90) | 40/67 (60) |
| S. mitis group[a] | 6/7 (86) | 10/12 (83) |
| CDC coryneform group G | 7/7 (100) | 1/2 (50) |
| S. salivarius | 3/3 (100) | 2/2 (100) |

[a]In this analysis, S. mitis group includes only isolates identified as S. mitis or S. mitis group.

Lack of Fluoroquinolone Resistance Development During Study 433

A total of 122 pathogens isolated at or above threshold at Visit 2 or Visit 3 (29 besifloxacin treated, 93 vehicle treated) were determined by PFGE analysis to be genetically concordant. MIC testing of all 122 genetically concordant isolate pairs indicated that susceptibility of Visit 2 or Visit 3 isolates did not increase by more than 2-fold for any of the tested fluoroquinolones, including besifloxacin.

Efficacy Conclusions for Study 433

Overall, in patients with culture-confirmed bacterial conjunctivitis, results from the primary efficacy endpoints, clinical resolution and bacterial eradication by Visit 2 (Day 5±1 day), demonstrated that besifloxacin ophthalmic suspension had efficacy outcomes that are significantly superior to those observed with vehicle. Furthermore, besifloxacin showed potent antimicrobial activity against a wide range of organisms.

Study 434

Results

Incidence of Baseline Pathogens

Comparable to Studies 373 and 433, a wide range of baseline pathogens were encountered. Again, organisms with the highest incidence included *S. pneumoniae, H. influenzae, S. aureus,* and *S. epidermidis,* as well as various other streptococci, staphylococci, and *corynebacteria* (Table 23).

TABLE 23

Baseline Pathogens With Incidence ≧1% in Species-Specific Study Eyes Across All Treatment Groups-Study 434 Besifloxacin vs Vigamox

| Organism | Incidence,[a] n (%) |
|---|---|
| H. influenzae | 169 (24.2) |
| S. pneumoniae | 122 (17.5) |
| S. aureus | 115 (16.5) |
| S. epidermidis | 70 (10.0) |
| S. mitis group[b] | 33 (4.7) |
| CDC coryneform group G | 18 (2.6) |
| S. oralis | 10 (1.4) |
| Aerococcus viridans | 8 (1.1) |
| C. pseudodiphtheriticum | 7 (1.0) |
| S. lugdunensis | 7 (1.0) |
| Moraxella catarrhalis | 7 (1.0) |
| Streptococcus sp.[c] | 7 (1.0) |

[a]Among 699 species-specific study eye pathogens at baseline (Visit 1).
[b]In this analysis, S. mitis group includes only isolates identified as S. mitis or S. mitis group.
[c]Species name could not be determined.

Clinical Resolution

Results for clinical resolution by 2 clinical signs/indices (conjunctival discharge and bulbar conjunctival injection) at Visit 2 (Day 5±1) and Visit 3 (Day 8 or 9) are summarized in Table 24. At Visit 2 (primary efficacy endpoint), when missing values and discontinued patients were imputed as clinical resolution failures, besifloxacin ophthalmic suspension was non-inferior to Vigamox for clinical resolution based on the 95% confidence interval (CI) of the difference (58.3% vs 59.4%, respectively; 95% CI, ±9.48%, 7.29%), and there was no statistically significant difference in clinical resolution between the 2 treatment groups (p=0.8601, exact Pearson chi-squared test p=0.6520, CMH adjusted for center effects).

At Visit 3, when missing values and discontinued patients were imputed as clinical resolution failures, besifloxacin ophthalmic suspension was non-inferior to Vigamox for clinical resolution based on the 95% CI of the difference (84.5% vs 84.0%, respectively; 95% CI, −5.67%, 6.75%), and there was no statistically significant difference in clinical resolution between the 2 treatment groups p=0.9055, exact Pearson chi-squared test, or p=0.5014, CMH adjusted for center effects).

TABLE 24

Clinical Resolution by 2 Indices at Visit 2 (Day 5 ± 1) and Visit 3 (Day 8 or 9) (mITT, Culture-confirmed, As Treated)-Study 434

| | Primary Endpoint Visit 2 (Day 5 ± 1) | | Visit 3 (Day 8 or 9) | |
|---|---|---|---|---|
| Clinical Resolution (2 indices)[a] | Besifloxacin (N = 252) | Vigamox (N = 281) | Besifloxacin (N = 252) | Vigamox (N = 281) |
| Yes, n (%) | 147 (58.3) | 167 (59.4) | 213 (84.5) | 236 (84.0) |
| No, n (%) | 105 (41.7) | 114 (40.6) | 39 (15.5) | 45 (16.0) |

TABLE 24-continued

Clinical Resolution by 2 Indices at Visit 2 (Day 5 ± 1) and Visit 3
(Day 8 or 9) (mITT, Culture-confirmed, As Treated)-Study 434

| Clinical Resolution (2 indices)[a] | Primary Endpoint Visit 2 (Day 5 ± 1) | | Visit 3 (Day 8 or 9) | |
|---|---|---|---|---|
| | Besifloxacin (N = 252) | Vigamox (N = 281) | Besifloxacin (N = 252) | Vigamox (N = 281) |
| p value[b] | 0.8601/0.6520 | | 0.9055/0.5014 | |
| 95% CI[c] | (−9.48, 7.29) | | (−5.67, 6.75) | |

CI = Confidence interval;
CMH = Cochran-Mantel-Haenszel.
[a]Ocular discharge and bulbar conjunctival injection
[b]p values from exact Pearson chi-squared test/CMH test stratified by center, respectively.
[c]Difference calculated as besifloxacin minus Vigamox. Positive values favor besifloxacin.
Note:
Percentages are based on the number of patients indicated in the column heading (culture-confirmed as-treated population).

Microbial Eradication

Results for eradication of baseline bacterial infection at Visit 2 (Day 5±1) and Visit 3 (Day 8 or 9) are summarized in Table 25. At Visit 2, when missing values and discontinued patients were imputed as microbial eradication failures, besifloxacin ophthalmic suspension was non-inferior to Vigamox for microbial eradication based on the 95% CI of the difference (93.3% vs 91.1%, respectively; 95% CI, −2.44%, 6.74%), and there was no statistically significant difference between the 2 treatment groups (p=0.4217, exact Pearson chi-squared test or p=0.1238, CMH adjusted for center effects). At Visit 3, when missing values and discontinued patients were imputed as microbial eradication failures, besifloxacin ophthalmic suspension was non-inferior to Vigamox for microbial eradication based on the 95% CI of the difference (87.3% vs 84.7%, respectively; 95% CI, ±3.32%, 8.54%), and there was no statistically significant difference in microbial eradication between the 2 treatment groups (p=0.4544, exact Pearson chi-squared test or p=0.0608, CMH adjusted for center effects).

TABLE 25

Microbial Eradication at Visit 2 (Day 5 ± 1) and Visit 3 (Day 8 or 9) (mITT, Culture-confirmed, As Treated)-Study 434

| Microbial Eradication (missing or discontinued patients imputed as 'no') | Primary Endpoint Visit 2 (Day 5 ± 1) | | Visit 3 (Day 8 or 9) | |
|---|---|---|---|---|
| | Besifloxacin (N = 252) | Vigamox (N = 281) | Besifloxacin (N = 252) | Vigamox (N = 281) |
| Yes, n (%) | 235 (93.3) | 256 (91.1) | 220 (87.3) | 238 (84.7) |
| No, n (%) | 17 (6.7) | 25 (8.9) | 32 (12.7) | 43 (15.3) |
| p value[a] | 0.4217/0.1238 | | 0.4544/0.0608 | |
| 95% CI[b] | (−2.44, 6.74) | | (−3.32, 8.53) | |

CI = Confidence interval;
CMH = Cochran-Mantel-Haenszel.
[a]p values from exact Pearson chi-squared test/CMH test stratified by center, respectively.
[b]Difference calculated as besifloxacin minus Vigamox. Positive values favor besifloxacin.
Note:
Percentages are based on the number of patients indicated in the column heading (culture-confirmed, 'as-treated' population).

Microbial Eradication of Baseline Pathogens

Microbial eradication at Visit 3 (Day 8 or 9) is shown by baseline pathogens in Table 26 for besifloxacin versus Vigamox. Comparable to the other 2 studies, these results show a broad-spectrum nature of the microbial eradication with besifloxacin, very high eradication rates independent of the Gram-stain characteristics, and high eradication rates for the most prevalent organisms encountered.

TABLE 26

Microbial Eradication at Visit 2 (Day 5 ± 1) by Baseline Species-Specific Study Eye Isolates With Incidence ≧1% in Study 434 - Besifloxacin vs Vigamox

| | Isolates eradicated/encountered (%) | |
|---|---|---|
| Pathogen | Besifloxacin | Vigamox |
| Gram-positive isolates | 209/227 (92) | 219/244 (90) |
| Gram-negative isolates | 98/102 (96) | 120/126 (95) |
| H. influenzae | 75/79 (95) | 85/90 (94) |
| S. aureus | 50/59 (85) | 48/56 (86) |
| S. epidermidis | 27/29 (93) | 36/41 (88) |
| S. pneumoniae | 53/56 (95) | 60/66 (91) |
| S. mitis group[a] | 10/11 (91) | 13/14 (93) |
| CDC coryneform group G | 6/7 (86) | 11/11 (100) |
| S. oralis | 6/6 (100) | 3/4 (75) |
| C. pseudodiphtheriticum | 5/5 (100) | 2/2 (100) |
| S. lugdunensis | 4/4 (100) | 3/3 (100) |

[a]In this analysis, S. mitis group includes only isolates identified as S. mitis or S. mitis group.

Lack of Fluoroquinolone Resistance Development During Study 434

A total of 65 pathogens isolated at or above threshold at Visit 2 or Visit 3 (26 besifloxacin treated, 39 Vigamox treated) were determined by PFGE analysis to be genetically concordant. MIC testing of all 65 genetically concordant isolate pairs indicated that susceptibility of Visit 2 or Visit 3 isolates did not increase by more than 2-fold for any of the tested fluoroquinolones, including besifloxacin.

Efficacy Conclusions for Study 434

In patients with culture-confirmed bacterial conjunctivitis, results for the primary efficacy endpoints, clinical resolution and microbial eradication at Visit 2 (Day 5±1), demonstrated that besifloxacin ophthalmic suspension was non-inferior to Vigamox, suggesting that treatment of bacterial conjunctivitis with besifloxacin ophthalmic suspension will produce efficacy outcomes that are similar to those observed when treating with Vigamox.

Clinical Microbiology

Integrated Summary of Species-Specific Microbiological Eradication

In this section, only key microbial efficacy data from the integrated analyses of Studies 373, 433, and 434 are presented. For the species-specific microbiological eradication, baseline pathogens with levels at or above threshold were analyzed as treated.

In the original analyses for Study 373, data were analyzed using the baseline-designated study eye (ie, clinically diagnosed bacterial conjunctivitis based on 3 clinical signs—conjunctival discharge, bulbar conjunctival injection and palpebral conjunctival injection), and unlike analyses for Studies 433 and 434, no data were analyzed using a species-specific study eye designation. To facilitate comparison of the results between studies, additional analyses were completed to the final report for Study 373, using a species-specific study eye designation for the summary of clinical and microbial outcome for each Gram-positive and each Gram-negative bacterial species. In these additional analyses, the definition of the species-specific study eye was the same as that used for clinical Studies 433 and 434.

Statistical Analysis and Data Tabulation Implications

All integrated analyses are based on the culture-confirmed (mITT) study population (n=1041), which includes all ITT patients from Study 373 and all mITT patients from Studies 433 and 434. The mITT study population included all patients in the study population for whom baseline cultures in at least 1 eye indicated bacteria levels at or above threshold for any accepted ocular species.

The integration of the microbiological data across the three studies included the integration of Visit 2 data (Day 4±1 day for Study 373 and Day 5±1 day for Studies 433 and 434) and the integration of Visit 3 (Day 8 or 9 for Studies 373, 433, and 434). In these integrated analyses, the primary endpoint visit is Visit 2 and the secondary endpoint visit is Visit 3, which is consistent with the analyses of individual Studies 433 and 434 but is different from the analyses of Study 373 where Visit 3 was considered the primary endpoint visit. Microbiological eradication was identically defined among the three studies.

Overall Analysis of Studies 373, 433, and 434

Results from species-specific study eyes at Visit 2 or 3 in the culture-confirmed (mITT) as-treated population (or the equivalent ITT population in Study 373) will be described. In vitro susceptibilities to besifloxacin and other antibacterial agents were determined for all isolates regardless of treatment group.

Incidence of Key Organisms at Baseline

The baseline distribution of key pathogens across Studies 373, 433, and 434 is shown in Table 32. In total, 1324 bacterial isolates were reported; Study 373 contributed 145 isolates, Study 433 contributed 480 isolates, and Study 434 contributed 699 isolates. Study 434 included 95 isolates from Asian sites, accounting for 7.2% (95/1324) of isolates from all three studies or 13.6% (95/699) of isolates from Study 434. The contribution of isolates per treatment group was as follows: besifloxacin, 656 (49.5%) isolates; Vigamox®, 370 (27.9%) isolates; and vehicle, 298 (22.5%) isolates. This ratio was also observed in most cases at the species level. The besifloxacin treatment arm was included in all 3 studies being integrated, the vehicle treatment arm was part of Studies 373 and 433, and the Vigamox® treatment arm was part of Study 434 only. Asian sites were part of Study 434 only.

Of the 1324 bacterial isolates, 886 (66.9%) were Gram-positive, while the remaining 438 (33.1%) were Gram-negative. The most frequently isolated organisms across all 3 studies were *Haemophilus influenzae* (344 isolates, 26.0%), *Streptococcus pneumoniae* (302 isolates, 22.8%), *Staphylococcus aureus* (190 isolates, 14.4%), *Staphylococcus epidermidis* (111 isolates, 8.4%), *Streptococcus mitis* group (65 isolates, 4.9%), CDC coryneform group G (29 isolates, 2.2%), and *Streptococcus oralis* (18 isolates, 1.4%) (Table 27).

TABLE 27

Baseline Pathogens With Incidence ≥1% in Species-Specific Study Eyes-Studies 373, 433, 434 Combined

| Organism | Study 373 (N = 145) | Study 433 (N = 480) | Study 434 (N = 699) | Total (N = 1324) |
|---|---|---|---|---|
| *H. influenzae* | 46 (31.7) | 129 (26.9) | 169 (24.2) | 344 (26.0) |
| *S. pneumoniae* | 40 (27.6) | 140 (29.2) | 122 (17.5) | 302 (22.8) |
| *S. aureus* | 20 (13.8) | 55 (11.5) | 115 (16.5) | 190 (14.4) |
| *S. epidermidis* | 7 (4.8) | 34 (7.1) | 70 (10.0) | 111 (8.4) |
| *S. mitis* group[a] | 3 (2.1) | 29 (6.0) | 33 (4.7) | 65 (4.9) |
| CDC coryneform group G | 2 (1.4) | 9 (1.9) | 18 (2.6) | 29 (2.2) |
| *S. oralis* | 4 (2.8) | 4 (0.8) | 10 (1.4) | 18 (1.4) |

Incidence, n (%)

[a] In this analysis, *S. mitis* group includes only isolates identified as *S. mitis* or *S. mitis* group.

Antibacterial Susceptibility of Baseline Pathogens

Susceptibility testing of clinical trial isolates was performed for besifloxacin and comparator test agents. Isolates cultured in Studies 373, 433, and 434 yielded besifloxacin susceptibility patterns similar to those observed in the non-clinical studies. A total of 1324 isolates were recovered from patients at baseline (Visit 1) in the culture-confirmed (mITT), as-treated population species-specific study eye across all treatment groups. Overall $MIC_{50}/MIC_{90}$ values for the 1324 isolates of all species from all treatment groups combined were 0.06/0.25 µg/mL for besifloxacin and 0.125/0.5 µg/mL for moxifloxacin. $MIC_{90}$ values were slightly higher in isolates from Asia: 1 µg/mL for besifloxacin and 2 µg/mL for moxifloxacin. Of the 1324 bacterial isolates, 886 (66.9%) were Gram-positive, while the remaining 438 (33.1%) were Gram-negative (Table 28). The besifloxacin $MIC_{50}/MIC_{90}$ values were 0.06/0.25 µg/mL for Gram-positive bacteria and 0.03/0.5 µg/mL for Gram-negative bacteria.

As discussed previously, patients' fellow eyes could contribute species-specific study eye isolates if that species was not already present in that patient's study eye. Table 28 outlines the contribution of fellow eyes to the number of species-specific study eye isolates.

TABLE 28

Distribution of Baseline Species-Specific Pathogens Across Baseline-Designated Study Eyes and Baseline-Designated Fellow Eyes in the Culture-Positive, As-Treated Population

| Organism | Besifloxacin | Vigamox | Vehicle | Overall |
|---|---|---|---|---|
| All species | 40/656 (6.1) | 18/370 (4.9) | 15/298 (5.0) | 73/1324 (5.5) |
| Gram-positive | 34/447 (7.6) | 15/244 (6.1) | 14/195 (7.2) | 63/886 (7.1) |
| Gram-negative | 6/209 (2.9) | 3/126 (2.4) | 1/103 (1.0) | 10/438 (2.3) |
| *H. influenzae* | 2/167 (1.2) | 2/90 (2.2) | 1/87 (1.1) | 5/344 (1.5) |
| *S. aureus* | 7/93 (7.5) | 0/56 (0) | 0/41 (0) | 7/190 (3.7) |
| *S. epidermidis* | 6/50 (12.0) | 6/41 (14.6) | 4/20 (20.0) | 16/111 (14.4) |
| *S. pneumoniae* | 1/153 (0.7) | 0/66 (0) | 0/83 (0) | 1/302 (0.3) |

Baseline-Designated Fellow Eye/All Species-Specific Study Eye Isolates (%)

MIC Distribution for Besifloxacin and Comparator Test Agents for Selected Species from Combined Besifloxacin, Vehicle, and Vigamox Treatment Groups The antibacterial susceptibility profile of each Visit 1 bacterial isolate was determined for besifloxacin and other antimicrobials. The integrated MIC range, $MIC_{50}$ and $MIC_{90}$ values of selected species for besifloxacin, azithromycin, ciprofloxacin, gatifloxacin, levofloxacin, moxifloxacin, and ofloxacin are provided in Table 29.

The same improved efficacy of besifloxacin was observed for the multi-drug resistant strains. In fact, in this case with no exceptions, besifloxacin was more active than or equal to the competitor drugs.

Clinical isolates of *S. aureus* and *S. epidermidis* were grouped according to their susceptibility to oxacillin and ciprofloxacin. Table 30 shows the MIC data for besifloxacin and comparator antimicrobial agents for those isolates.

TABLE 29

In Vitro Activity of Besifloxacin and Comparators Against Key Organisms-
Studies 373, 433, and 434 Species-Specific Study Eye Isolates

| Organism | Phenotype | N | MIC (µg/mL) | BESI | AZITH | CIPRO | GATI | LEVO | MOXI | OFLOX |
|---|---|---|---|---|---|---|---|---|---|---|
| All | All | 1324 | Range | 0.008-8 | 0.008->8 | ≦0.004->8 | ≦0.004->8 | ≦0.004- | ≦0.004->8 | 0.008- |
|  |  |  | $MIC_{50}$ | 0.06 | 2 | 0.25 | 0.125 | 0.25 | 0.125 | 0.5 |
|  |  |  | $MIC_{90}$ | 0.25 | >8 | 2 | 0.5 | 1 | 0.5 | 2 |
| Gram-positive | All | 886 | Range | 0.008-8 | 0.008->8 | 0.015->8 | 0.008->8 | 0.008->8 | 0.008->8 | 0.008- |
|  |  |  | $MIC_{50}$ | 0.06 | 1 | 0.5 | 0.25 | 0.5 | 0.125 | 1 |
|  |  |  | $MIC_{90}$ | 0.25 | >8 | 4 | 1 | 2 | 0.5 | 4 |
| Gram-negative | All | 438 | Range | 0.008-8 | 0.015->8 | ≦0.004->8 | ≦0.004-8 | ≦0.004-8 | ≦0.004-8 | 0.015- |
|  |  |  | $MIC_{50}$ | 0.03 | 2 | 0.015 | 0.015 | 0.03 | 0.03 | 0.03 |
|  |  |  | $MIC_{90}$ | 0.5 | >8 | 0.125 | 0.25 | 0.125 | 0.25 | 0.25 |
| CDC coryneform group G |  | 29 | Range | 0.008-2 | 0.06->8 | 0.03-8 | 0.03-8 | 0.06->8 | 0.03->8 | 0.125- |
|  |  |  | $MIC_{50}$ | 0.015 | 0.125 | 0.06 | 0.06 | 0.06 | 0.03 | 0.125 |
|  |  |  | $MIC_{90}$ | 0.125 | >8 | 0.5 | 0.5 | 1 | 0.25 | 2 |
| Corynebacterium pseudodiphtheriticum |  | 8 | Range | 0.015-0.25 | 0.125->8 | 0.03-1 | 0.06-0.5 | 0.06-1 | 0.03-0.5 | 0.125-2 |
|  |  |  | $MIC_{50}$ | 0.25 | >8 | 0.5 | 0.5 | 0.5 | 0.25 | 1 |
|  |  |  | $MIC_{90}$ | — | — | — | — | — | — | — |
| Corynebacterium striatum |  | 8 | Range | 0.015-0.25 | 0.06->8 | 0.015-8 | 0.015-2 | 0.03-4 | 0.015-2 | 0.125- |
|  |  |  | $MIC_{50}$ | 0.015 | 0.125 | 0.03 | 0.03 | 0.06 | 0.03 | 0.125 |
|  |  |  | $MIC_{90}$ | — | — | — | — | — | — | — |
| Haemophilus influenzae | All | 344 | Range | 0.008-0.5 | 0.015->8 | ≦0.004-1 | ≦0.004-0.5 | ≦0.004-1 | 0.008-1 | 0.015- |
|  |  |  | $MIC_{50}$ | 0.03 | 2 | 0.015 | 0.015 | 0.03 | 0.03 | 0.03 |
|  |  |  | $MIC_{90}$ | 0.06 | 4 | 0.015 | 0.03 | 0.03 | 0.06 | 0.06 |
| Moraxella lacunata[a] |  | 9 | Range |  |  |  |  |  |  |  |
|  |  |  | $MIC_{50}$ |  |  |  |  |  |  |  |
|  |  |  | $MIC_{90}$ |  |  |  |  |  |  |  |
| Staphylococcus aureus | All | 190 | Range | 0.008-8 | 0.06->8 | 0.06->8 | 0.03->8 | 0.03->8 | 0.03->8 | 0.125- |
|  |  |  | $MIC_{50}$ | 0.03 | 2 | 0.5 | 0.125 | 0.25 | 0.06 | 0.5 |
|  |  |  | $MIC_{90}$ | 0.5 | >8 | >8 | 4 | 8 | 2 | >8 |
| Staphylococcus epidermidis | All | 111 | Range | 0.03-4 | 0.5->8 | 0.125->8 | 0.06->8 | 0.125->8 | 0.06->8 | 0.25 |
|  |  |  | $MIC_{50}$ | 0.06 | 1 | 0.25 | 0.125 | 0.25 | 0.125 | 0.5 |
|  |  |  | $MIC_{90}$ | 0.5 | >8 | >8 | 2 | 8 | 4 | >8 |
| Staphylococcus hominis |  | 9 | Range | 0.03-0.5 | 1->8 | 0.125-8 | 0.06-2 | 0.125-4 | 0.06-1 | 0.25 |
|  |  |  | $MIC_{50}$ | 0.06 | 4 | 0.125 | 0.125 | 0.125 | 0.06 | 0.25 |
|  |  |  | $MIC_{90}$ | — | — | — | — | — | — | — |
| Staphylococcus lugdunensis |  | 8 | Range | 0.06-0.5 | 0.015->8 | 0.25-8 | 0.25-2 | 0.25-2 | 0.125-2 | 0.5- |
|  |  |  | $MIC_{50}$ | 0.125 | 0.5 | 0.25 | 0.25 | 0.25 | 0.25 | 1 |
|  |  |  | $MIC_{90}$ | — | — | — | — | — | — | — |
| Streptococcus mitis[b] |  | 20 | Range | 0.06-0.25 | 0.06-8 | 0.25-4 | 0.25-1 | 0.5-2 | 0.06-0.5 | 1-4 |
|  |  |  | $MIC_{50}$ | 0.125 | 2 | 1 | 0.5 | 1 | 0.125 | 2 |
|  |  |  | $MIC_{90}$ | 0.125 | 4 | 2 | 1 | 1 | 0.25 | 2 |
| Streptococcus mitis group |  | 45 | Range | 0.03->8 | 0.3->8 | 0.06->8 | 0.06-2 | 0.125->8 | 0.03-2 | 0.25 |
|  |  |  | $MIC_{50}$ | 0.125 | 2 | 1 | 0.5 | 1 | 0.125 | 2 |
|  |  |  | $MIC_{90}$ | 0.25 | 8 | 4 | 0.5 | 2 | 0.25 | 4 |
| Streptococcus oralis |  | 18 | Range | 0.015-0.25 | 0.06->8 | 0.03-4 | 0.03-1 | 0.125-2 | 0.015-0.5 | 0.125 |
|  |  |  | $MIC_{50}$ | 0.125 | 4 | 2 | 0.5 | 1 | 0.25 | 2 |
|  |  |  | $MIC_{90}$ | 0.25 | >8 | 4 | 1 | 2 | 0.25 | 4 |
| Streptococcus pneumoniae | All | 302 | Range | 0.03-0.25 | 0.06->8 | 0.125->8 | 0.125-1 | 0.125-2 | 0.06-1 | 0.5- |
|  |  |  | $MIC_{50}$ | 0.06 | 0.125 | 0.5 | 0.25 | 0.5 | 0.125 | 1 |
|  |  |  | $MIC_{90}$ | 0.125 | >8 | 1 | 0.5 | 1 | 0.125 | 2 |
| Streptococcus salivarius |  | 9 | Range | 0.06-0.25 | 0.06->8 | 1-2 | 0.5-2 | 1-2 | 0.125-1 | 2-4 |
|  |  |  | $MIC_{50}$ | 0.125 | 8 | 2 | 0.5 | 1 | 0.25 | 2 |
|  |  |  | $MIC_{90}$ | — | — | — | — | — | — | — |

[a]No MIC values could be determined using standard test methods.
[b]In this table, *S. mitis* and *S. mitis* group are listed separately.

TABLE 30

In Vitro ($MIC_{90}$) Activity versus Resistant Staphylococcal Isolates-Studies 373, 433, and 434

| Pathogen | N | $MIC_{90}$ (μg/mL) | | | |
|---|---|---|---|---|---|
| | | Besifloxacin | Moxifloxacin | Gatifloxacin | Azithromycin |
| *S. aureus* | | | | | |
| MSSA-CS | 144 | 0.06 | 0.125 | 0.25 | >8 |
| MRSA-CS[a] | 9 | 0.06[a] | 0.06[a] | 0.25[a] | >8[a] |
| MSSA-CR | 17 | 2 | 8 | >8 | >8 |
| MRSA-CR | 17 | 4 | >8 | >8 | >8 |
| *S. epidermidis* | | | | | |
| MSSE-CS | 50 | 0.06 | 0.125 | 0.25 | >8 |
| MRSE-CS | 27 | 0.06 | 0.125 | 0.25 | >8 |
| MSSE-CR | 10 | 1 | 8 | 8 | >8 |
| MRSE-CR | 24 | 4 | >8 | >8 | >8 |

CR = Ciprofloxacin resistant;
CS = Ciprofloxacin susceptible.
[a]Due to limited isolates, highest MIC value is given.

Analysis on Organism-By-Organism Basis for Key Organisms

Overall, 86 bacterial conjunctival pathogenic species were isolated at baseline at or above threshold from species-specific study eyes and identified during the conduct of Studies 373, 433, and 434. Within the besifloxacin ophthalmic suspension treatment group, organisms with >10 isolates (in order of prevalence) included *H. influenzae, S. pneumoniae, S. aureus, S. epidermidis, S. mitis* group, CDC coryneform group G, and *Streptococcus oralis*. These species were termed Key Organisms.

Globally (US and Asia sites combined), microbial eradication rates for all species combined were 92.2% in the besifloxacin treatment group, 61.4% in the vehicle treatment group, and 91.6% in the Vigamox treatment group at Visit 2. At Visit 3, the corresponding numbers were 88.4%, 72.5%, and 85.7%, respectively (Table 31).

TABLE 31

Integrated Species-Specific Microbial Eradication Rates in Culture-confirmed, As-Treated Population (Global)

| Organism | Besifloxacin | | Vehicle | | Vigamox | |
|---|---|---|---|---|---|---|
| | Visit 2 | Visit 3 | Visit 2 | Visit 3 | Visit 2 | Visit 3 |
| All species | 606/656 | 580/656 | 183/298 | 216/298 | 339/370 | 317/370 |
| | (92.2%) | (88.4%) | (61.4%) | (72.5%) | (91.6%) | (85.7%) |
| Gram-positive | 412/447 | 392/447 | 114/195 | 140/195 | 219/244 | 211/244 |
| | (92.2%) | (87.7%) | (58.5%) | (71.8%) | (89.8%) | (86.5%) |
| Gram-negative | 193/209 | 188/209 | 69/103 | 76/103 | 120/126 | 106/126 |
| | (92.3%) | (90.0%) | (67.0%) | (73.8%) | (95.2%) | (84.1%) |
| CDC coryneform group G | 15/16 | 15/16 | 1/2 | 2/2 | 11/11 | 11/11 |
| | (93.8%) | (93.8%) | (50.0%) | (100.0%) | (100.0%) | (100.0%) |
| *C. pseudodiphtheriticum* | 6/6 | 6/6 | 0/0 | 0/0 | 2/2 | 2/2 |
| | (100.0%) | (100.0%) | 0 | 0 | (100.0%) | (100.0%) |
| *C. striatum* | 5/5 | 5/5 | 0/0 | 0/0 | 2/3 | 3/3 |
| | (100.0%) | (100.0%) | 0 | 0 | (66.7%) | (100.0%) |
| *H. influenzae* | 152/167 | 148/167 | 56/87 | 64/87 | 85/90 | 79/90 |
| | (91.0%) | (88.6%) | (64.4%) | (73.6%) | (94.4%) | (87.8%) |
| *M. lacunata* | 5/5 | 4/5 | 2/3 | 3/3 | 1/1 | 1/1 |
| | (100.0%) | (80.0%) | (66.7%) | (100.0%) | (100.0%) | (100.0%) |
| *S. aureus* | 81/93 | 78/93 | 16/41 | 20/41 | 48/56 | 46/56 |
| | (87.1%) | (83.9%) | (39.0%) | (48.8%) | (85.7%) | (82.1%) |
| *S. epidermidis* | 47/50 | 44/50 | 11/20 | 15/20 | 36/41 | 32/41 |
| | (94.0%) | (88.0%) | (55.0%) | (75.0%) | (87.8%) | (78.0%) |
| *S. hominis* | 5/6 | 6/6 | 1/2 | 1/2 | 1/1 | 1/1 |
| | (83.3%) | (100.0%) | (50.0%) | (50.0%) | (100.0%) | (100.0%) |
| *S. lugdunensis* | 5/5 | 5/5 | 0/0 | 0/0 | 3/3 | 2/3 |
| | (100.0%) | (100.0%) | 0 | 0 | (100.0%) | (66.7%) |
| *S. mitis* group[a] | 17/19 | 16/19 | 10/12 | 10/12 | 13/14 | 13/14 |
| | (89.5%) | (84.2%) | (83.3%) | (83.3%) | (92.9%) | (92.9%) |
| *S. oralis* | 10/11 | 8/11 | 2/3 | 2/3 | 3/4 | 3/4 |
| | (90.9%) | (72.7%) | (66.7%) | (66.7%) | (75.0%) | (75.0%) |

TABLE 31-continued

Integrated Species-Specific Microbial Eradication Rates in Culture-confirmed, As-Treated Population (Global)

| Organism | Besifloxacin | | Vehicle | | Vigamox | |
|---|---|---|---|---|---|---|
| | Visit 2 | Visit 3 | Visit 2 | Visit 3 | Visit 2 | Visit 3 |
| S. pneumoniae | 142/153 (92.8%) | 132/153 (86.3%) | 47/83 (56.6%) | 61/83 (73.5%) | 60/66 (90.9%) | 57/66 (86.4%) |
| S. salivarius | 5/5 (100.0%) | 4/5 (80.0%) | 2/2 (100.0%) | 2/2 (100.0%) | 2/2 (100.0%) | 2/2 (100.0%) |

Note:
Visit 2 was defined as Day 4 ± 1 in Study 373 and as Day 5 ± 1 in Studies 433 and 434; Visit 3 was defined as Day 8 or 9 in all 3 studies.
[a]In this analysis, S. mitis group includes only isolates identified as S. mitis or S. mitis group.

Graphic representations of the microbial eradication relative to the besifloxacin MIC distribution are shown in FIGS. 3 to 6 for H. influenzae, S. aureus, S. epidermidis, and S. pneumoniae.

Species-Specific Microbiological Eradication Failures

Isolate pairs from eyes with the same species at or above threshold at both baseline and follow-up visits were evaluated by Pulsed Field Gel Electrophoresis (PFGE) analysis to (i) distinguish new infections from recurrence and (ii) determine if any microbial eradication failures were correlated with antimicrobial resistance development during the study period. Concordant (similar) PFGE results for 2 clinical isolates suggest that the bacteria are closely related and belong to the same strain. The finding of two concordant isolates at baseline and follow-up with ≧4-fold increase in MIC values would have suggested the development of antimicrobial resistance during the study period; however, this finding was not observed. Strains with discordant PFGE fingerprints are not closely related, suggesting that one strain was replaced by another between baseline and the follow-up visit. In several instances, microbial eradication failures were the result of infection with a discordant strain.

In summary, microbial eradication failures were not a predictor of clinical resolution outcomes. No correlation was observed between bacterial species and microbial eradication failure other than the prevalence of the organism within the overall population of bacterial conjunctivitis isolates. Failures were the result of the persistence of the baseline (Visit 1) strain or re-infection with discordant strains of the same species. Analyses of the antibacterial susceptibility data showed that in no case did baseline strains develop resistance to besifloxacin or other fluoroquinolone test agents during the treatment period. The combined PFGE and susceptibility data did not indicate development of fluoroquinolone resistance for any isolates in the besifloxacin, Vigamox®, or vehicle treatment groups across Studies 373, 433, and 434.

Summary of Integrated Clinical Microbiological Results

The primary objective of this integrated analysis was to evaluate the clinical microbial efficacy of besifloxacin ophthalmic suspension, 0.6%, compared to either vehicle or Vigamox, administered TID for 5 days in the treatment of bacterial conjunctivitis.

Studies 373, 433, and 434 were large, controlled studies conducted according to Good Clinical Practices. Sites from both the United States and Asia were included in Study 434. In general, the US and Asian sites were similar regarding isolates, phenotypes, and sensitivities.

From a microbiological perspective, the baseline pathogen distribution was similar across the besifloxacin ophthalmic suspension, vehicle, and Vigamox® treatment groups.

The relative frequency of organisms isolated at threshold levels or higher from these studies, H. influenzae, S. pneumoniae, S. aureus, and S. epidermidis, were similar to previous reports in patients with bacterial conjunctivitis.

Besifloxacin was active against a wide range of organisms, including antimicrobial-resistant strains. Overall, the sensitivities of the pathogens obtained from patients in the besifloxacin ophthalmic suspension treatment group were similar to those obtained from patients in the Vigamox® or vehicle treatment groups (these included resistant phenotypes). Furthermore, no besifloxacin or moxifloxacin resistant strains emerged in any of the 3 clinical studies.

In these controlled studies, besifloxacin ophthalmic suspension showed potent antimicrobial activity against a wide range of organisms, similar to the comparator fluoroquinolone. These data indicate that treatment of bacterial conjunctivitis with besifloxacin ophthalmic suspension will produceclinically effective microbial eradication rates.

Analysis of Clinical Information Relevant to Dosing Recommendations

In each of the 3 controlled studies (Studies 373, 433, and 434), patients instilled one drop of besifloxacin ophthalmic suspension in the affected eye(s) TID for 5 days. Patients were instructed to invert the closed bottle and shake once prior to administering the drug. The 0.6% concentration of besifloxacin and TID dosing is supported by the PK/PD relationship analysis and data from the extensive preclinical and clinical development program.

Studies were conducted to assess the PK/PD relationship of besifloxacin ophthalmic suspension, 0.6%, from PK studies generated in humans along with the in vitro microbial efficacy (PD) data ($MIC_{90}$ values) generated from several prominent microorganisms isolated from patients with bacterial conjunctivitis. In addition, the effect of protein binding on besifloxacin PK/PD ratios also is reported for comparison to address the potential impact of protein binding on the microbial activity of besifloxacin. The results of this modeling exercise demonstrated that topical ocular application of 0.6% besifloxacin ophthalmic suspension results in high therapeutic levels of besifloxacin in human tears, which remained above the $MIC_{90}$ value for most ocular pathogens up to 24 hours after dosing (mean $C_{24h}$=1.60±2.28 µg/g). The PK/PD ratios for these bacteria obtained after a simulated TID dosing scheme demonstrate that the $C_{max}/MIC_{90}$ and $AUC_{24}/MIC_{90}$ ratios are high, and substantially above the target values published for fluoroquinolones (ie, $C_{max}/MIC_{90}$ ratio of >10 and $AUC/MIC_{90}$ ratio of >100-125 regardless of whether total besifloxacin concentrations or only unbound besifloxacin concentrations are considered. Taken together, these results provide a PK/PD-based rationale that supports the favorable efficacy observed with besifloxacin in the treatment of bacterial conjunctivitis.

Persistence of Efficacy and/or Tolerance Effects

Bacterial conjunctivitis is an acute, self-limiting disease. In the clinical safety and efficacy trials conducted in support of this application, patients were dosed TID for 5 days with besifloxacin ophthalmic suspension versus vehicle (Studies 373 and 433) or Vigamox (Study 434). Rates of clinical resolution and microbial eradication observed at Visit 2 (Day 4±1 for Study 373 and Day 5±1 for Studies 433 and 434) and Visit 3 (Day 8 or 9 for all studies) provided no evidence of tolerance or resistance.

Summary of Clinical Efficacy

Results from these studies demonstrated that besifloxacin ophthalmic suspension administered TID for 5 days was superior to vehicle and non-inferior to Vigamox. The primary efficacy endpoints were met for each of these studies.

Summary of Safety

Across all 3 studies, no statistically significant differences were observed between treatment groups for visual acuity, biomicroscopy/slit lamp examination, or opthalmoscopy.

In addition, ocular and systemic PK studies have demonstrated that besifloxacin ophthalmic suspension has high ocular retention ($\geq 1.6$ μg/g for at least 24 hours after a single dose), low systemic exposure (<0.5 ng/mL), and no effect on corneal endothelial cell density.

Benefit/Risk Summary

The three clinical efficacy and safety studies (Studies 373, 433, and 434) conducted to support the application for marketing authorization demonstrated superior outcomes for besifloxacin ophthalmic suspension administered TID for 5 days versus its vehicle for both clinical resolution and microbial eradication and clinical and microbial outcomes at least similar to those observed with Vigamox®. Besifloxacin ophthalmic suspension administered TID for 5 days showed broad-spectrum eradication for Gram-negative and Gram-positive organisms, potent activity against resistant strains, and improved $MIC_{90}$ values versus comparator antibacterial agents used to treat bacterial conjunctivitis. These findings, along with evidence supporting the low propensity of besifloxacin ophthalmic suspension for resistance development, demonstrate the benefit of this drug for the treatment of bacterial conjunctivitis.

Overall, besifloxacin ophthalmic suspension has been shown to be safe and well tolerated. Clinical studies have demonstrated low systemic exposure following administration of single and multiple doses of besifloxacin ophthalmic suspension and no corneal endothelial cell density changes.

In summary, besifloxacin ophthalmic suspension has been shown to be safe and effective for the treatment of bacterial conjunctivitis in adequate and well-controlled studies. Besifloxacin ophthalmic suspension fits the ideal profile for the treatment of bacterial conjunctivitis because it is a local ocular treatment for a local ocular disease, has convenient dosing that is efficacious, a long dwell time on the ocular surface, broad-spectrum antibacterial activity against a wide variety of pathogens, potent microbial eradication, bactericidal activity, low propensity for resistance development, and a favorable safety profile.

Other Non-Limiting Embodiments of the Present Inventions

Other non-limiting embodiments of the formulation of the present invention are disclosed below.

Example 1

| Ingredient | Amount (% w/v) |
| --- | --- |
| besifloxacin | 0.3 |
| sorbitol | 1 |
| tyloxapol | 0.2 |
| carbopol 71G NF | 0.8 |
| glycerin | 2.5 |
| EDTA disodium | 0.2 |
| benzalkonium chloride | 0.001 |

The above materials are mixed together in a high-speed mixer (e.g., at speed of 200-1000 rpm) for about 10-60 minutes to produce a composition of the present invention. The mixer may be provided with a water cooling jacket to control temperature in the range from 18-35° C. The composition may be further sterilized using any well-known techniques in the pharmaceutical art before packaging.

Example 2

| Ingredient | Amount (% w/v) |
| --- | --- |
| besifloxacin | 0.6 |
| mannitol | 1 |
| polysotbate 80 | 2 |
| sodium alginate | 0.25 |
| propylene glycol | 0.6 |
| sodium chloride | 0.2 |
| benzalkonium chloride | 0.001 |

The materials are mixed together as described in Example 1 to produce another composition of the present invention.

Example 3

| Ingredient | Amount (% w/v) |
| --- | --- |
| besifloxacin | 0.8 |
| polyoxyethylene hydrogenated castor oil | 0.5 |
| polysotbate 60 | 2.5 |
| Perlmulen TR-1 NF | 0.5 |
| propylene glycol | 0.6 |
| sodium chloride | 0.2 |
| EDTA disodium | 0.2 |
| benzalkonium chloride | 0.001 |

The materials are mixed together as described in Example 1 to produce another composition of the present invention.

Example 4

| Ingredient | Amount (% w/v) |
| --- | --- |
| besifloxacin HCl | 0.65 |
| mannitol | 1 |
| polysotbate 80 | 2 |
| chondroitin sulfate | 0.4 |
| carboxymethyl cellulose | 0.25 |
| propylene glycol | 0.6 |
| sodium chloride | 0.2 |
| stabilized oxychloro complex (preservative) | 0.01 |

The materials are mixed together as described in Example 1 to produce another composition of the present invention.

REFERENCES

Allen, G. P., Kaatz, G. W., & Rybak, M. J. (2004). In vitro activities of mutant prevention concentration-targeted concentrations of fluoroquinolones against *Staphylococcus aureus* in a pharmacodynamic model. *Int J Antimicrob Agents*, 24(2), 150-160.

Bergogne-Berezin, E. (2002). Clinical role of protein binding of quinolones. *Clin Pharmacokinet*, 41(10), 741-750.

Brook, I., Pettit, T. H., Martin, W. J., & Finegold, S. M. (1979). Anaerobic and aerobic bacteriology of acute conjunctivitis. *Ann Opthalmol*, 11(3), 389-393.

Craig, W. A., & Ebert, S. C. (1989). Protein binding and its significance in antibacterial therapy. *Infect Dis Clin North Am*, 3(3), 407-414.

Diamant, J., Hwang, D G (1999). Therapy for bacterial conjunctivitis. *Opthalmol Clin North Am*, 12(1), 15-20.

Drusano, G. L. (1988). Role of pharmacokinetics in the outcome of infections. *Antimicrob Agents Chemother*, 32(3), 289-297.

Gigliotti, F., Williams, W. T., Hayden, F. G., Hendley, J. O., Benjamin, J., Dickens, M., et al. (1981). Etiology of acute conjunctivitis in children. *J Pediatr*, 98(4), 531-536.

Gocke, E. (1991). Mechanism of quinolone mutagenicity in bacteria. *Mutat Res*, 248(1), 135-143.

Hammond, R. W., & Edmondson, W. (1997). Treatment of ocular bacterial infections: an update. *J Am Optom Assoc*, 68(3), 178-187.

Hermsen, E. D., Hovde, L. B., Konstantinides, G. N., & Rotschafer, J. C. (2005). Mutant prevention concentrations of ABT-492, levofloxacin, moxifloxacin, and gatifloxacin against three common respiratory pathogens. *Antimicrob Agents Chemother*, 49(4), 1633-1635.

Jensen, H. G., & Felix, C. (1998). In vitro antibiotic susceptibilities of ocular isolates in North and South America. In Vitro Antibiotic Testing Group. *Cornea*, 17(1), 79-87.

Leeming, J. P. (1999). Treatment of ocular infections with topical antibacterials. *Clin Pharmacokinet*, 37(5), 351-360.

Leibowitz, H. M. (1991). Antibacterial effectiveness of ciprofloxacin 0.3% ophthalmic solution in the treatment of bacterial conjunctivitis. *Am J Opthalmol*, 112(4 Supply, 29S-33S.

Lorian, V., ed. (2005). *Antibiotics in Laboratory Medicine: Making a Difference* (5th ed.). Philadelphia, Pa.: Lippincott Williams & Wilkins.

Merrikin, D. J., Briant, J., & Rolinson, G. N. (1983). Effect of protein binding on antibiotic activity in vivo. *J Antimicrob Chemother*, 11(3), 233-238.

Metzler, K., Hansen, G. M., Hedlin, P., Harding, E., Drlica, K., & Blondeau, J. M. (2004). Comparison of minimal inhibitory and mutant prevention drug concentrations of 4 fluoroquinolones against clinical isolates of methicillin-susceptible and -resistant *Staphylococcus aureus*. *Int J Antimicrob Agents*, 24(2), 161-167.

Nightingale, C. H. (2005). Future in vitro and animal studies: development of pharmacokinetic and pharmacodynamic efficacy predictors for tissue-based antibiotics. *Pharmacotherapy*, 25(12 Pt 2), 146S-149S.

Sheikh, A., & Hurwitz, B. (2006). Antibiotics versus placebo for acute bacterial conjunctivitis. *Cochrane Database Syst Rev*(2), CD001211.

Smith, H. J., Walters, M., Hisanaga, T., nand, G. G., & Hoban, D. J. (2004). Mutant prevention concentrations for single-step fluoroquinolone-resistant mutants of wild-type, efflux-positive, or ParC or GyrA mutation-containing *Streptococcus pneumoniae* isolates. *Antimicrob Agents Chemother*, 48(10), 3954-3958.

Turnidge, J. (1999). Pharmacokinetics and pharmacodynamics of fluoroquinolones. *Drugs*, 58 Suppl 2, 29-36.

Wright, D. H., Brown, G. H., Peterson, M. L., & Rotschafer, J. C. (2000). Application of fluoroquinolone pharmacodynamics. *J Antimicrob Chemother*, 46(5), 669-683.

Zeitlinger, M., Sauermann, R., Fille, M., Hausdorfer, J., Leitner, I., & Muller, M. (2008). Plasma protein binding of fluoroquinolones affects antimicrobial activity. *J Antimicrob Chemother*, 61(3), 561-567.

While specific embodiments of the present invention have been described in the foregoing, it will be appreciated by those skilled in the art that many equivalents, modifications, substitutions, and variations may be made thereto without departing from the spirit and scope of the invention as defined in the appended claims.

What is claimed is:

1. A method for treating or controlling bacterial conjunctivitis in a human subject, the method comprising administering to said human subject a composition comprising besifloxacin at a concentration of 0.6% (weight by volume) at a frequency of two, three, or four times per day for 5-10 days in an amount effective for said treating or controlling, wherein said bacterial conjunctivitis is caused by a bacterium selected from the group consisting of *Staphylococcus aureus, Staphylococcus epidermidis, Staphylococcus haemolyticus, Staphylococcus warneri, Staphylococus hominis, Morganella morganii, Prevotella* spp., and *Fusobacterium* against which an $MIC_{90}$ of gatifloxacin or moxifloxacin is at least 4 µg/mL.

2. The method of claim 1, wherein said bacterium is *S. aureus* or *S. epidermidis* resistant to both methicillin and ciprofloxacin.

3. A method for treating or controlling bacterial conjunctivitis in a human subject, the method comprising administering to said human subject a composition comprising besifloxacin at a concentration of 0.6% (weight by volume) at a frequency of two, three, or four times per day for 5-10 days in an amount effective for said treating or controlling, wherein said bacterial conjunctivitis is caused by a bacterium selected from the group consisting of *Staphylococcus aureus, Staphylococcus epidermidis, Staphylococcus haemolyticus, Staphylococcus warneri, Staphylococus hominis, Staphylococcus lugdunensis*, and *Morganella morganii* against which an $MIC_{90}$ of gatifloxacin or moxifloxacin is at least 4 µg/mL, and an $MIC_{90}$ of ciprofloxacin is greater than 8 µg/mL.

* * * * *